(12) United States Patent
Penfield et al.

(10) Patent No.: US 11,847,600 B1
(45) Date of Patent: *Dec. 19, 2023

(54) METHOD AND SYSTEM FOR INDUSTRIAL ERGONOMICS RISK ROOT-CAUSE ANALYSIS AND MANAGEMENT USING ARTIFICIAL INTELLIGENCE ORIENTED NATURAL LANGUAGE PROCESSING TECHNIQUES

(71) Applicant: VelocityEHS Holdings Inc., Chicago, IL (US)

(72) Inventors: Julia Penfield, Seattle, WA (US); Pulkit Trushantkumar Parikh, Toronto (CA); Richard Thomas Barker, West Chester, OH (US)

(73) Assignee: VelocityEHS Holdings Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,396

(22) Filed: Aug. 4, 2023

Related U.S. Application Data

(63) Continuation of application No. 18/133,902, filed on Apr. 12, 2023, now Pat. No. 11,763,235.

(51) Int. Cl.
*G06Q 10/00* (2023.01)
*G06Q 10/0635* (2023.01)
*G06F 40/30* (2020.01)
*G06F 40/205* (2020.01)

(52) U.S. Cl.
CPC ....... *G06Q 10/0635* (2013.01); *G06F 40/205* (2020.01); *G06F 40/30* (2020.01)

(58) Field of Classification Search
CPC .................................................. G06Q 10/0635
See application file for complete search history.

(56) References Cited

U.S. PATENT DOCUMENTS

| 11,324,439 B2 | 5/2022 | Diaz-Arias et al. |
| 11,482,048 B1 | 10/2022 | Diaz-Arias et al. |
| 11,516,158 B1 | 11/2022 | Luzhnica et al. |
| 11,580,150 B1 * | 2/2023 | Gutta .................. G06N 3/0442 |

(Continued)

FOREIGN PATENT DOCUMENTS

| WO | 2022183138 A2 | 9/2022 |
| WO | 2023023379 A1 | 2/2023 |

*Primary Examiner* — Satwant K Singh
(74) *Attorney, Agent, or Firm* — K&L Gates LLP

(57) ABSTRACT

A system for identifying industrial ergonomics risk root-causes and providing risk control actions, comprising: a computing device configured to obtain textual information describing a series of tasks of a job and forces being exerted during the series of tasks; and a computing server system configured to receive and process the textual information to generate a set of textual entry to correspond to a unique identifier of the job, identify nouns and verbs in the set of textual entry via natural language processing techniques, perform dependency parsing and part-of-speech tagging to associate each identified verb in the set of textual entry with a root noun in order to identify action-object pairs and unpaired actions, determine ergonomic risk root-causes based at least upon the action-object pairs and the unpaired actions in the set of textual entry, and provide ergonomic risk control recommendations to mitigate the ergonomic risk root-causes.

20 Claims, 19 Drawing Sheets

(56) References Cited

U.S. PATENT DOCUMENTS

| | | | |
|---|---|---|---|
| 11,720,615 B2* | 8/2023 | Gutta | G06F 40/186 |
| | | | 715/256 |
| 11,763,078 B2* | 9/2023 | Wilson-Thomas | G06F 40/166 |
| | | | 715/816 |
| 11,763,235 B1* | 9/2023 | Penfield | G06F 40/205 |
| | | | 704/9 |
| 2020/0012670 A1* | 1/2020 | Heckmann | G06N 5/02 |
| 2021/0294970 A1 | 9/2021 | Bender et al. | |
| 2022/0079510 A1 | 3/2022 | Robillard et al. | |
| 2022/0207392 A1* | 6/2022 | Hou | G10L 15/26 |
| 2022/0245354 A1 | 8/2022 | Mackay et al. | |
| 2022/0358286 A1 | 11/2022 | Wilson-Thomas et al. | |
| 2022/0386942 A1 | 12/2022 | Diaz-Arias et al. | |

\* cited by examiner

| Columns that uniquely identify a job | Task description |
|---|---|
| Job 1 identifiers | Lifting rods |
| Job 3 identifiers | Lower door |
| Job 4 identifiers | Pushing tote |

202 points to the header "Columns that uniquely identify a job"; 204 points to "Task description"

FIG. 2A

| Columns that uniquely identify a job | Force description |
|---|---|
| Job 1 identifiers | Pushing rack |
| Job 2 identifiers | Lifting box |
| Job 1 identifiers | Shoveling |

206 points to the header "Columns that uniquely identify a job"; 208 points to "Force description"

FIG. 2B

| Columns that uniquely identify a job | Force descriptions | Task descriptions |
|---|---|---|
| Job 1 identifiers | Pushing rack, Shoveling | Lifting rods |
| Job 2 identifiers | Lifting box | |
| Job 3 identifiers | | Lower door |
| Job 4 identifiers | | Pushing tote |

FIG. 5

| User descriptions of forces associated with a job if any | User descriptions of tasks associated with a job if any | Action-objects pairs identified | Unpaired actions identified |
|---|---|---|---|
| Pinch Grip to Handle Parts, Lift/ Lower Parts, Pull to Close Washer Lid (Both) | Moving parts from conveyor into washer | (pinch, grip), (handle, part), (lift, part), (close, washer lid), (move, part) | pull |
| Using channel lock to close strain relief part | | (use, channel lock), (close, strain relief part) | |
| | Lift Housing-Magnet sub-assembly to Press | (lift, housing magnet sub assembly) | press |
| Push tape down on box, Squeeze to lift filter | | (push, tape), (lift, filter) | squeeze |
| Push Chassis on rail, Lift Chassis from bin, Pinch and push wire connector, Pull bin while it is in the bin to unlock chassis | Handling frame - bin to line | (push, chassis), (lift, chassis), (pinch, wire connector), (pull, bin), (unlock, chassis), (handle, frame) | |
| Upward force applied to screw gun attaching lid | | (apply, upward force), (attach, lid) | |
| Pinch to grab paper, Final fold box, Lift unit from paint line, Push box through taper, Packing material | unhook of gear box from paint line conveyor | (grab, paper), (lift, unit), (push, box), (unhook, gear box) | pinch |
| Install rubber shelf bumper grommet | | (install, rubber shelf bumper grommet) | |
| | Loading raw stock, Lifting pelican cases, Lifting parts into customer packaging, Lifting cardboard boxes | (load, raw stock), (lift, case), (lift, part), (lift, cardboard box) | |
| Hndle Tool, Unload the H-Frame, Unload the track | | (unload, h frame), (unload, track) | |

FIG. 6

| Descriptions of Forces Exerted | Example 1 | Example 2 | Example 3 | Example 4 |
|---|---|---|---|---|
| | Moving a cart, Sticking a strip, Drilling holes, Tightening screws | Operating a hose | Lifting a box | Moving a part, Turning an object |
| Descriptions of Tasks Performed | Join parts, Assembling | Wash mechanical parts | Lift a box | Attach a part |

FIG. 11

| Action-Objects Pairs | Example 1 | Example 2 | Example 3 | Example 4 |
|---|---|---|---|---|
| | (move, cart), (stick, strip), (tighten, screw), (join, part) | (operate, hose), (wash, mechanical part) | (lift, box) | (move, part), (turn, object), (attach, part) |
| Unpaired Actions | Assemble | | | |

FIG. 12

| Clusters identified from all actions inferred across jobs (Examples 1-4) | Clusters identified from all objects inferred across jobs (Examples 1-4) |
|---|---|
| push, stick, tighten | screw, hose, box |
| operate, turn | mechanical part, object |
| attach, assemble | part |
| join | cart |
| Wash | strip |
| lift | |

FIG. 13

Cause #1 Edit

Cart grip is too low
↓
Handle is too low

Description

Category
Equipment/Tool Design

Status
Not Addressed

Apply to Another Body Region

Suggested Controls

☐ Install a vertical handle

☐ Provide cart with optimal handle heights

☐ Raise handle

☐ Custom Control

FIG. 15(A)

| | | | | | | | | |
|---|---|---|---|---|---|---|---|---|
| | | | | | | | Projected Summary | |
| Improvement # | Improvement Title | Responsible Person | Cost | ROI | Control | Priority | Targeted Date | Status |
| | Provide cart with optimal handle heights | | | | | | | View |
| Add a new improvement » | | | | | | | | Add |
| Design Guidelines for Ergonomics | | | | | | | | |

Cause #1    Edit

Control location is too low

Description

Category
Equipment/Tool Design

Status
Not Addressed

Apply to Another Body Region

Suggested Controls

☐ Raise control

☐ [Custom Control]

[Add to Improvements]

FIG. 17(A)

| Improvement # | Improvement Title | Responsible Person | Cost | ROI | Control | Priority | Targeted Date | Status |
|---|---|---|---|---|---|---|---|---|
| | Raise control | | | | | | | View |
| Add a new improvement » | | | | | | | | Add |
| Design Guidelines for Ergonomics | | | | | | | | |

Cause #1 Edit

Parts are presented, delivered, or stored too low

↓

Pallet/container is delivered at floor height

Description

Category

Workstation Layout

Status

Not Addressed

Apply to Another Body Region

Suggested Controls

☐ Provide a fixed-height pallet stand

☐ Provide a pallet lift table

☐ Provide a portable lift cart or pallet lift

FIG. 19(A)

| Improvement # | Improvement Title | Responsible Person | Cost | ROI | Control | Priority | Targeted Date | Status | |
|---|---|---|---|---|---|---|---|---|---|
| | Provide a portable lift cart or pallet lift | | | | | | | | View |
| Add a new improvement » | | | | | | | | | Add |
| Design Guidelines for Ergonomics | | | | | | | | | |

METHOD AND SYSTEM FOR INDUSTRIAL ERGONOMICS RISK ROOT-CAUSE ANALYSIS AND MANAGEMENT USING ARTIFICIAL INTELLIGENCE ORIENTED NATURAL LANGUAGE PROCESSING TECHNIQUES

CROSS REFERENCE TO RELATED APPLICATION

The present application is a continuation of U.S. application Ser. No. 18/133,902, filed on Apr. 12, 2023, entitled "METHOD AND SYSTEM FOR INDUSTRIAL ERGONOMICS RISK ROOT-CAUSE ANALYSIS AND MANAGEMENT USING ARTIFICIAL INTELLIGENCE ORIENTED NATURAL LANGUAGE PROCESSING TECHNIQUES," the disclosures of which are incorporated herein by reference.

FIELD OF TECHNOLOGY

The present disclosure generally relates to methods and systems for analyzing ergonomic risk factors at workplaces, and more particularly relates to methods and systems configured to analyze industrial ergonomics risk root-causes based at least upon relevant textual information using natural language processing (NLP) techniques and provide risk control actions accordingly.

BACKGROUND

Musculoskeletal disorders generally refer to a common type of work related illness and have been recognized as a major cause of absence among working populations. Conditions that are caused or exacerbated by activities at the workplace are often labeled as work-related musculoskeletal disorders (WMSDs) and are characterized by discomfort of nerves, tendons, muscles, and supporting structures of the body. WMSDs can affect the ability of workers to perform the required occupational activities which could have a negative effect on productivity. WMSDs and their relation to lost workdays in the health care industry have been studied and found to account for a substantial portion of the WMSD burden on society. In order to minimize the risk of workers developing WMSDs, it is crucial to conduct an effective workplace risk assessment from an ergonomic standpoint and identify the root-causes of the risk. For example, there may exist certain unstructured textual information (e.g., physical forces involved in the jobs performed by workers and the tasks carried out, notes, text-heavy documents and websites, images, video files, chatbots, audio streams, social media posts, etc.) that may be leveraged for the ergonomic risk root cause analysis.

Accordingly, there is a need to develop a method and system configured with artificial intelligence oriented natural language processing (NLP) capabilities to identify actions and any associated objects from unstructured textual information relating to tasks and forces associated with workers' jobs for analyzing and managing WMSD ergonomics risk root-causes.

SUMMARY

In one aspect, the present disclosure provides a system deployed within a Cloud-based communication network, the system comprising a computing device which includes a non-transitory computer-readable storage medium configured to store an application program; and a processor coupled to the non-transitory computer-readable storage medium and configured to control a plurality of modules to execute instructions of the application program to obtain textual information describing a series of tasks of a job and forces being exerted during the series of tasks. The system further comprises a computing server system configured to receive the textual information, process the textual information to generate a set of textual entry to correspond to a unique identifier of the job, wherein the set of textual entry includes a list of tasks and a list of forces associated with the job, identify nouns and verbs in the set of textual entry via natural language processing techniques, perform dependency parsing and part-of-speech tagging to associate each identified verb in the set of textual entry with a root noun, identify action-object pairs and unpaired actions in the set of textual entry based at least upon results of the dependency parsing and the part-of-speech tagging, determine ergonomic risk root-causes based at least upon the action-object pairs and the unpaired actions in the set of textual entry, and provide ergonomic risk control recommendations to mitigate the ergonomic risk root-causes.

In one embodiment, the computing server system may be further configured to receive video signals of the worker performing the job at the workplace; process the video signals to determine joint locations of the worker; calculate joint angles for each of a plurality of body regions of the worker based on the joint locations; calculate, based at least upon the joint angles and the forces being exerted during the series of tasks, a risk score for each of the plurality of body regions of the worker in each of a plurality of risk categories, wherein the plurality of risk categories comprise an awkward posture category, a duration category, a frequency category, and a force category; calculate a risk rating for each of the plurality of body regions of the worker based on the risk score for each of the plurality of body regions of the worker in each of the plurality of risk categories; and determine the ergonomic risk root-causes for each of the plurality of body regions of the worker based at least upon the risk rating.

In another embodiment, the computing server system may be configured to identify the nouns in the set of textual entry by at least filtering out phrases whose root nouns are subjects, and removing noun phrases containing any verbs.

In another embodiment, the computing server system may be configured to perform the dependency parsing to associate each identified verb in the set of textual entry with the root noun by at least determining a position of the root noun to each identified verb in a dependency tree. For example, the computing server system may traverse the dependency tree to identify a parent or child node of each identified verb based at least on a relative position between the root noun and each identified verb.

In yet another embodiment, the computing server system may be further configured to remove duplicated actions or objects from the action-object pairs and the unpaired actions.

In accordance with another aspect, the present disclosure may relate to a computer-implemented method, comprising obtaining, by a processor of a computing device deployed within a Cloud-based communication network, textual information describing a series of tasks of a job and forces being exerted during the series of tasks; receiving, by a computing server system deployed within the Cloud-based communication network, the textual information; processing, by the computing server system, the textual information to generate a set of textual entry to correspond to a unique identifier of the job, wherein the set of textual entry includes a list of tasks and a list of forces associated with the job; identifying, by the computing server system, nouns and verbs in the set of textual entry via natural language processing techniques; performing, by the computing server system, dependency parsing and part-of-speech tagging to associate each identified verb in the set of textual entry with a root noun; identifying, by the computing server system, action-object pairs and unpaired actions in the set of textual entry based at least upon results of the dependency parsing and the part-of-speech tagging; determining, by the computing server system, ergonomic risk root-causes based at least upon the action-object pairs and the unpaired actions in the set of textual entry; and providing, by the computing server system, ergonomic risk control recommendations to mitigate the ergonomic risk root-causes.

In one embodiment, the method may further comprise obtaining, by the computing server system, video signals of the worker performing the job at the workplace; processing, by the computing server system, the video signals to determine joint locations of the worker; calculating, the computing server system, joint angles for each of a plurality of body regions of the worker based on the joint locations; calculating, the computing server system, based at least upon the joint angles and the forces being exerted during the series of tasks, a risk score for each of the plurality of body regions of the worker in each of a plurality of risk categories, wherein the plurality of risk categories comprise an awkward posture category, a duration category, a frequency category, and a force category; calculating, the computing server system, a risk rating for each of the plurality of body regions of the worker based on the risk score for each of the plurality of body regions of the worker in each of the plurality of risk categories; and determining, the computing server system, the ergonomic risk root-causes for each of the plurality of body regions of the worker based at least upon the risk rating. In one aspect, identifying the nouns in the set of textual entry may comprise filtering out phrases whose root nouns are subjects, and removing noun phrases containing any verbs.

In another embodiment, the method may also comprise performing, by the computing server system, the dependency parsing to associate each identified verb in the set of textual entry with the root noun by at least determining a position of the root noun to each identified verb in a dependency tree. For example, the dependency tree may be traversed to identify a parent or child node of each identified verb based at least on a relative position between the root noun and each identified verb. In yet another embodiment, the method may additionally comprise removing, by the computing server system, duplicated actions or objects from the action-object pairs and the unpaired actions.

Moreover, the present disclosure relates to a non-transitory computer readable medium storing computer executable instructions for a system deployed in a Cloud-based communication network, the instructions being configured for: obtaining, by a processor of a computing device deployed within a Cloud-based communication network, textual information describing a series of tasks of a job and forces being exerted during the series of tasks; receiving, by a computing server system deployed within the Cloud-based communication network, the textual information; processing, by the computing server system, the textual information to generate a set of textual entry to correspond to a unique identifier of the job, wherein the set of textual entry includes a list of tasks and a list of forces associated with the job; identifying, by the computing server system, nouns and verbs in the set of textual entry via natural language processing techniques; performing, by the computing server system, dependency parsing and part-of-speech tagging to associate each identified verb in the set of textual entry with a root noun; identifying, by the computing server system, action-object pairs and unpaired actions in the set of textual entry based at least upon results of the dependency parsing and the part-of-speech tagging; determining, by the computing server system, ergonomic risk root-causes based at least upon the action-object pairs and the unpaired actions in the set of textual entry; and providing, by the computing server system, ergonomic risk control recommendations to mitigate the ergonomic risk root-causes.

In one embodiment, the instructions for identifying the nouns in the set of textual entry comprise instructions for filtering out phrases whose root nouns are subjects, and removing noun phrases containing any verbs.

In one embodiment, the non-transitory computer readable medium further comprises instructions for identifying the nouns in the set of textual entry comprises instructions for filtering out phrases whose root nouns are subjects, and removing noun phrases containing any verbs; performing, by the computing server system, the dependency parsing to associate each identified verb in the set of textual entry with the root noun by at least determining a position of the root noun to each identified verb in a dependency tree; and traversing, by computing server system, the dependency tree to identify a parent or child node of each identified verb based at least on a relative position between the root noun and each identified verb. In addition, the non-transitory computer readable medium further comprises instructions for removing, the computing server system, duplicated actions or objects from the action-object pairs and the unpaired actions.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplary pointed out in the claims.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

FIGS. 2A and 2B respectively illustrate textual information describing a series of work activities of a job and forces being exerted during these work activities as inputs to the system of FIG. 1, according to an exemplary aspect of the present disclosure;

FIG. 5 illustrates a unification of the information of FIGS. 2A and 2B, according to an exemplary aspect of the present disclosure;

FIG. 6 illustrates action-object pairs and unpaired actions for each of 10 different jobs based at least upon user-provided textual descriptions of tasks associated with each job and/or forces associated with each job, according to an exemplary aspect of the present disclosure;

FIG. 11 illustrates a summary of textual information describing a series of work activities of 4 example jobs and forces being exerted during these work activities as inputs to the system of FIG. 1, according to an exemplary aspect of the present disclosure;

FIG. 12 illustrates action-object pairs and unpaired actions for each of the 4 example jobs based at least upon user-provided textual descriptions of tasks associated with each job and/or forces associated with each job, according to an exemplary aspect of the present disclosure;

FIG. 13 illustrates action and object clusters inferred across the 4 example jobs, according to an exemplary aspect of the present disclosure;

FIGS. 15(A) and 15(B) respectively illustrate example control suggestions for user selected root-causes regarding the first example job, according to an exemplary aspect of the present disclosure;

FIGS. 16(A), 16(B), 16(C) and 16(D) illustrate ergonomics risk root-cause identification results of a second example job based at least upon video signals of a worker performing the first job related to the extracted images/frames of FIGS. 8(A)-8(D) and textual information describing a series of work activities of the job and forces being exerted during these work activities, according to an exemplary aspect of the present disclosure;

FIGS. 17(A) and 17(B) respectively illustrate example control suggestions for user selected root-causes regarding the second example job, according to an exemplary aspect of the present disclosure;

FIGS. 18(A), 18(B), 18(C) and 18(D) illustrate ergonomics risk root-cause identification results of a third example job based at least upon video signals of a worker performing the first job related to the extracted images/frames of FIGS. 9(A)-9(D) and textual information describing a series of work activities of the job and forces being exerted during these work activities, according to an exemplary aspect of the present disclosure;

FIGS. 19(A) and 19(B) respectively illustrate example control suggestions for user selected root-causes regarding the third example job, according to an exemplary aspect of the present disclosure;

FIGS. 20(A), 20(B), 20(C) and 20(D) illustrate ergonomics risk root-cause identification results of a fourth example job based at least upon video signals of a worker performing the first job related to the extracted images/frames of FIGS. 9(A)-9(D) and textual information describing a series of work activities of the job and forces being exerted during these work activities, according to an exemplary aspect of the present disclosure;

FIGS. 21(A) and 21(B) respectively illustrate example control suggestions for user selected root-causes regarding the fourth example job, according to an exemplary aspect of the present disclosure.

DETAILED DESCRIPTION

Figure 1:
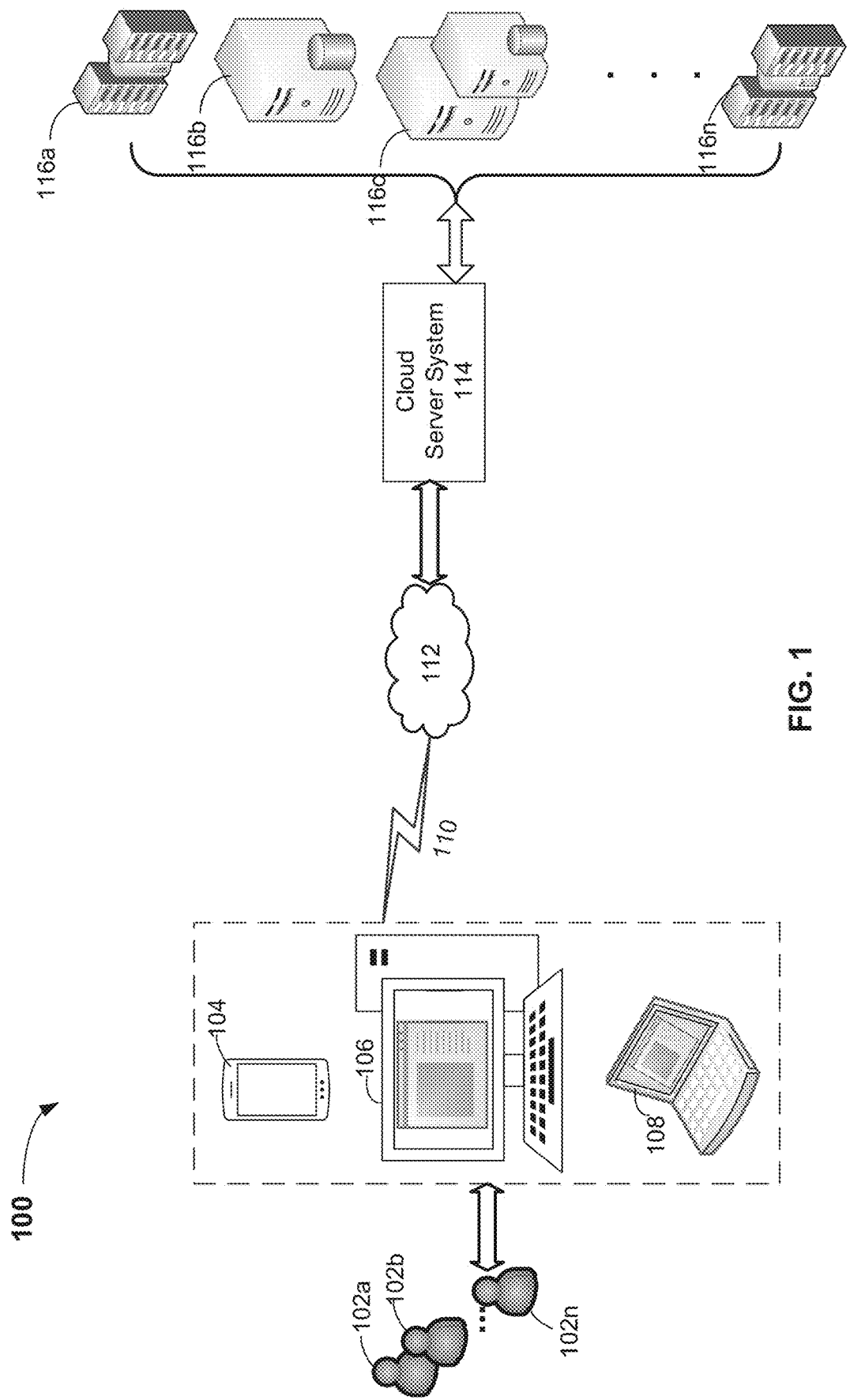
FIG. 1 illustrates an overall architecture of an automated industrial ergonomics risk assessment, ergonomics risk root-cause identification, and ergonomics risk control actions recommendation system, according to an exemplary aspect of the present disclosure.

Various aspects of the present disclosure will be described with reference to the drawings, wherein like reference numerals are used to refer to like elements throughout. In the following description, for purposes of explanation, numerous specific details are set forth in order to promote a thorough understanding of one or more aspects of the present disclosure. It may be evident in some or all instances, however, that any aspects described below can be practiced without adopting the specific design details described below.

Referring to FIG. 1, in accordance with aspects of the present disclosure, a system 100 deployed within a Cloud-based (and/or server-based) computing environment and communication network may be configured to provide relevant stakeholders 102a, 102b 102n (e.g., employers, safety professionals, etc.) with an ergonomics risk assessment of a workplace in any industrial setup. As will be described fully below, system 100 may be configured to identify the most likely root-causes of high ergonomics risk at the workplace based at least upon certain obtained unstructured textual information (e.g., job tasks being performed and forces being exerted) and provide recommended corrective risk control actions accordingly.

In one embodiment, an application, which may be a mobile or web-based application (e.g., native iOS or Android Apps), is downloaded and installed on a selected computing device or system 104, 106 or 108 for obtaining at least a video of a worker performing a job and textual information describing a series of work activities of the job and forces being exerted during these work activities. Computing device 104, 106 or 108 hosting the mobile or web-based application may be configured to connect, via suitable communication protocol 110 and network 112, with a remote Cloud server system 114 which may be configured to identify the physical actions performed and any objects associated with those actions from received textual information via artificial intelligence oriented NLP techniques in order to aid ergonomics experts (e.g., one of 102a, 102b . . . 102n) in identifying the root-causes of WMSD risks at the workplace efficiently. For example, part of speech (PoS) tagging, dependency parsing or any suitable NLP techniques may be utilized by the Cloud server system 114 to automatically identify the action-object pairs as well as the actions with no associated objects. Further, information inferred across jobs and frequently found actions and objects may be aggregated using distributional word embeddings and transformer-based deep neural networks in order to facilitate the grouping of actions and objects. System 100 of the present disclosure may be configured to combine all of the processed information with ergonomics expert's domain expertise to identify the most likely root-causes of WMSD risks at the workplace. For example, certain identified action and object pairs may be assigned the most likely root-causes, and each potential root-cause may be assigned at least one recommended control strategy for reducing a worker's exposure to WMSD risk.

It should be appreciated that each of the computing devices or systems 104, 106, 108 may comprise at least one of computing devices, servers, server farms, laptops, tablets, mobile devices, smart phones, smart watches, fitness tracker devices, cellular devices, gaming devices, media players, network enabled printers, routers, wireless access points, network appliances, storage systems, any suitable databases, gateway devices, smart home devices, virtual or augmented reality devices, or any other suitable devices that are deployed in the same or different communication networks of these computing devices and systems. The Cloud server system 114 may be configured to provide functionalities for any connected devices such as sharing data or provisioning resources among multiple client devices, or performing computations for each connected client device. The term "server" generally refers to a computing device or system, including processing hardware and process space(s), an associated storage medium such as a memory device or database, and, in some instances, at least one database application as is well known in the art. It should also be understood that "server system" and "server" are often used interchangeably herein.

In one embodiment, computing devices 104, 106, 108 and any connected computing devices of the system 100 may be configured to communicate with the Cloud server system 114 via a communication network 112 using suitable network connections and protocols 110. A communication network (e.g., communication network 112) may refer to a geographically distributed collection of computing devices or data points interconnected by communication links and segments for transporting signals and data therebetween. A protocol (e.g., protocol(s) 110) may refer to a set of rules defining how computing devices and networks may interact with each other, such as frame relay, internet protocol (IP), transmission control protocol (TCP), user datagram protocol (UDP), hypertext transfer protocol (HTTP). Many types of communication networks are available, ranging from local area networks (LANs), wide area networks (WANs), cellular networks, to overlay networks and software-defined networks (SDNs), a packet data network (e.g., the Internet), mobile telephone networks (e.g., cellular networks, such as 4 G or 5 G), Plain Old Telephone (POTS) networks, and wireless data networks (e.g., Institute of Electrical and Electronics Engineers (IEEE) 802.11 family of standards known as Wi-Fi®, WiGig®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2 P) networks, virtual private networks (VPN), Bluetooth, Near Field Communication (NFC), or any other suitable network. Computing devices 104, 106 and 108 may be configured to communicate in a peer to peer manner to replace, duplicate, supplement or extend the functionalities of communication network 112.

In one aspect, the Cloud server system 114 of the present disclosure may be configured to provide various computing services using shared resources. Cloud computing may generally include Internet-based computing in which computing resources are dynamically provisioned and allocated to each connected computing device or other devices on-demand, from a collection of resources available via the network or the Cloud. Cloud computing resources may include any type of resource, such as computing, storage, and networking. For instance, resources may include service devices (firewalls, deep packet inspectors, traffic monitors, load balancers, etc.), computing/processing devices (servers, CPUs, GPUs, random access memory, caches, etc.), and storage devices (e.g., network attached storages, storage area network devices, hard disk drives, solid-state devices, etc.). In addition, such resources may be used to support virtual networks, virtual machines, databases, applications, etc. The term "database," as used herein, may refer to a database (e.g., relational database management system (RDBMS) or structured query language (SQL) database), or may refer to any other data structure, such as, for example a comma separated values (CSV), tab-separated values (TSV), JavaScript Object Notation (JSON), eXtendible markup language (XML), TeXT (TXT) file, flat file, spreadsheet file, and/or any other widely used or proprietary format. In some embodiments, one or more of the databases or data sources may be implemented using one of relational databases, flat file databases, entity-relationship databases, object-oriented databases, hierarchical databases, network databases, NoSQL databases, and/or record-based databases.

Within the system 100, Cloud computing resources accessible via any suitable communication network (e.g., Internet) may include a private Cloud, a public Cloud, and/or a hybrid Cloud. Here, a private Cloud may be a Cloud infrastructure operated by an enterprise for use by the enterprise, while a public Cloud may refer to a Cloud infrastructure that provides services and resources over a network for public use. In a hybrid Cloud computing environment which uses a mix of on-premises, private Cloud and third-party, public Cloud services with orchestration between the two platforms, data and applications may move between private and public Clouds for greater flexibility and more deployment options. Some example public Cloud service providers may include Amazon (e.g., Amazon Web Services® (AWS)), IBM (e.g., IBM Cloud), Google (e.g., Google Cloud Platform), and Microsoft (e.g., Microsoft) Azure®. These providers provide Cloud services using computing and storage infrastructures at their respective data centers and access thereto is generally available via the Internet. Some Cloud service providers (e.g., Amazon AWS Direct Connect and Microsoft Azure ExpressRoute) may offer direct connect services and such connections typically require users to purchase or lease a private connection to a peering point offered by these Cloud providers.

The Cloud server system 114 of the present disclosure may be configured to connect with various data sources or services 116*a*, 116*b*, 116*c*, . . . 116*n*. In one embodiment, as will be described fully below, the Cloud server system 114 may be configured to generate a list of likely root-causes for identified high ergonomics risks that may be selected from the thousands of ergonomics assessments performed by ergonomics experts. One of the data sources or services

116*a*, 116*b*, 116*c*, . . . 116*n* may comprise a database of control options to use in job assessment reports provided during consulting projects over the past several decades. This database of controls may be used to identify potential controls associated with each specific root cause identified. These lists of likely root causes and controls may be supplemented by information from MSD cause and control charts developed for the United States Air Force (DTIC AD-A325515, AD-A325660, AD-A361230). For another example, one of the data sources or services 116*a*, 116*b*, 116*c*, . . . 116*n* may comprise an artificial intelligence based diagnostic system or an expert or knowledge based diagnostic or evaluation system for providing or optimizing recommendations that may include text, audio, video, and other rich media explanations.

In one preferred embodiment, a user (e.g., at least one of 102*a*, 102*b* . . . 102*n*) of system 100 of the present disclosure may be prompted to upload a video recording of a worker performing a job to the application hosted by one of the computing device or system 104, 106 or 108. In addition, the user may be prompted to enter textual descriptions of tasks being performed and any forces being exerted while performing those tasks. The Cloud server system 114 of system 100 may be configured to use relation extraction, NLP, and machine learning techniques to analyze the obtained textual information to determine action-object pairs and unpaired actions. Specifically, the Cloud server system 114 may convert unstructured textual data into structured textual data comprising at least actions and objects. This structure may be used for analyzing the key elements of textual input data of the system 100 as well as the relationship between these elements. For example, the Cloud server system 114 may initially determine a list of all actions that are highly relevant to job tasks being analyzed. Thereafter, multiple action-object pairs may be identified from the textual input data such that each pair comprises an action and an object associated with it. In the meantime, the Cloud server system 114 may identify unpaired actions where each of which has no associated object. The identified action-object pairs may be used by the Cloud server system 114 to map to the most likely root-causes. One or more risk control actions may be determined and presented to the user for each identified root-cause.

In one aspect, the Cloud server system 114 may be configured to partition a stream of textual input data (e.g., unstructured data and/or natural language text describing a series of work activities) into words, terms, sentences, symbols or other suitable discrete elements. For example, a list of actions-of-interest commonly used for ergonomics risk root-cause analysis may be pre-determined and the Cloud server system 114 may replace the actions extracted from the input textual data for which there are synonyms in this actions-of-interest list with the best synonyms. Further, the Cloud server system 114 may determine a list of all actions identified across all jobs, a list of all objects identified, a list of all action-object pairs, and a list of new actions (actions whose synonyms may be absent in the actions-of-interest list) along with the corresponding frequencies of occurrence. Additionally, a clustering of highly frequent actions and objects may be extracted by the Cloud server system 114 across all jobs. The parameters of clustering may be configured to limit the combinations of action-object pairs that ergonomists need to consider while carrying out root-cause analysis.

In addition to the video recording of a worker performing a job, the Cloud server system 114 may prompt the user (e.g., at least one of 102*a*, 102*b* . . . 102*n*) of system 100 to enter textual information describing a series of work activities of the job and forces being exerted during these work activities, as shown in FIGS. 2A and 2B, respectively. In one embodiment, as shown in FIG. 2A, the key column 202 in the task-related data from the standpoint of inferring actions and any associated objects may include information relating to a series of task activities of a specific job. General textual task descriptions 204 (e.g., lifting rods, lower door, pushing tote, etc.) may correspond to each identified task activity. The Cloud server system 114 may be configured to uniquely identify each task activity of a job via an identifier. That is, in one embodiment, each job processed by the system 100 of the present disclosure may be assigned a unique set of job identifiers when the job is initially input into the system 100. These job identifiers may uniquely identify each job, thereby grouping all the tasks and forces determined by the Cloud server system 114 with each job. Similarly, as shown in FIG. 2B, input textual data relating to forces exerted during a job may include a column 206 comprising information relating to a series of task activities of a specific job and general textual force descriptions 208 (e.g., pushing rack, lifting box, shoveling, etc.) corresponding to each identified task activity.

Figure 3:
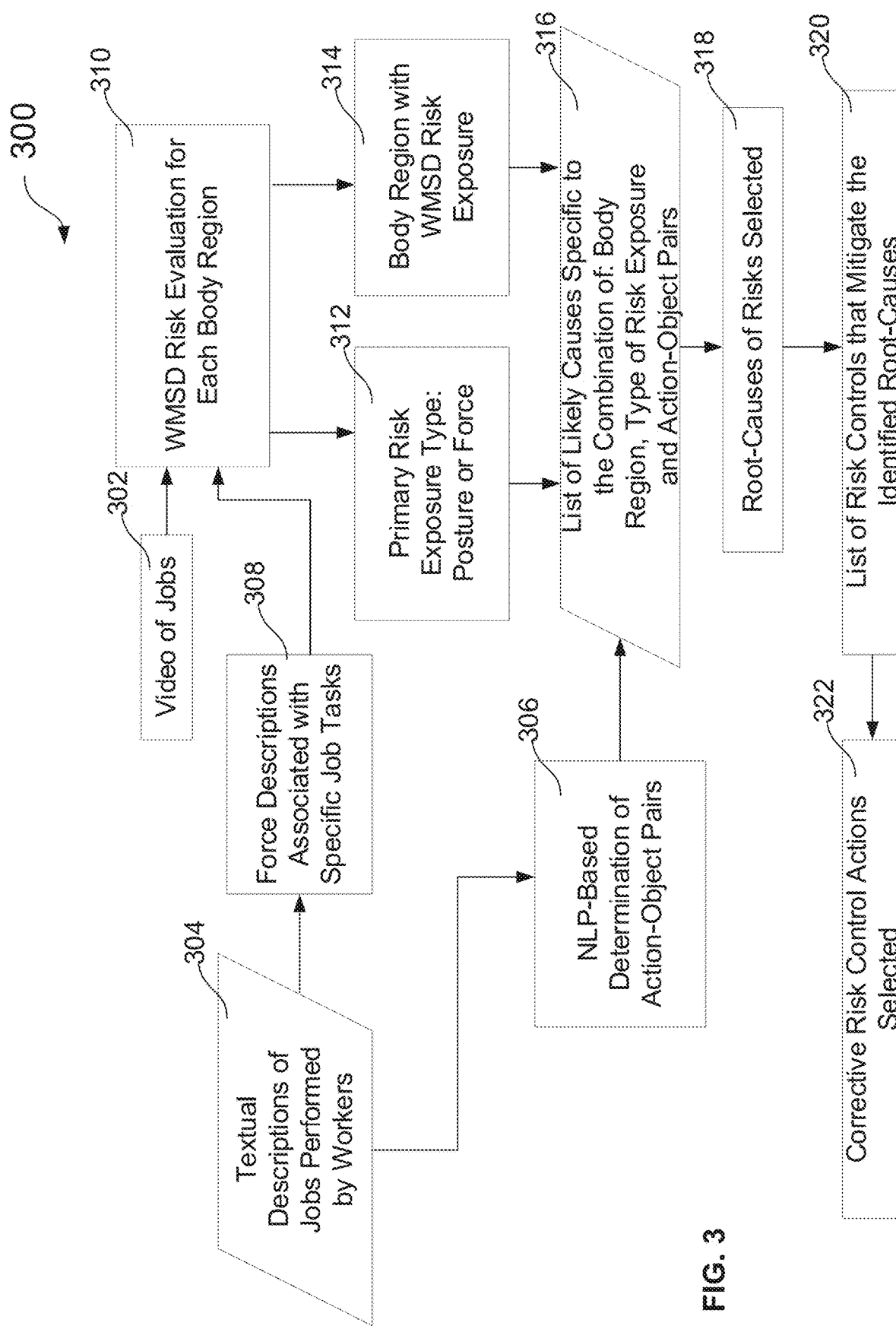
FIG. 3 illustrates an overall workflow of the system of FIG. 1, according to an exemplary aspect of the present disclosure.

FIG. 3 illustrates an example overall workflow 300 of the ergonomics risk root-cause analysis and risk controls recommendation system 100 of the present disclosure. As disclosed previously, input data required by the system 100 to provide the priority risk scores may include video signals 302 showing a worker performing a job and unstructured textual information 304 describing the job performed by the worker (e.g., one or more task activities being performed (FIG. 2A) and forces being exerted for each task activity (FIG. 2B)). In one aspect, the system 100 may be configured to use 306 relation extraction, NLP, and machine learning techniques to analyze the obtained textual information to determine action-object pairs and unpaired actions, which will be described fully below. On the other hand, the system 100 may be configured to utilize computer vision technology and deep learning framework to process the uploaded video signals 302 and force descriptions 308 associated with each job task to perform 310 WMSD risk analysis and generate risk evaluation results (e.g., risk levels) for each identified body region of the worker. Force descriptions 308 may include information related to a force direction, a force magnitude, and force textual descriptions. In one embodiment, the force direction may be selected from a plurality of pre-determined directions: "Hands Only," "Press Down," "Pull Down," "Pull In," "Push Out," "Pull Across," and "Lift/Lower." The system 100 may be configured to prompt the user to enter force magnitude information via the application installed on one of the computing devices 104, 106 or 108. In an important aspect, the system 100 may prompt the user to provide textual inputs describing the forces exerted during the job. The Cloud server system 114 may then be configured to determine primary risk exposure type (e.g., posture or force) 312 and identify body region(s) with WMSD risk exposure 314. In one aspect, the system 100 may be configured to generate 316 a list of likely root-causes specific to the combination of the identified body region(s) 314, type(s) of risk exposure 312, and action-object pairs 306 inferred from the unstructured textual inputs. Thereafter, the user of the system 100 may be prompted to select 318 the cause that most accurately addresses the force or posture issue. Alternatively, if none of the causes from the list applies, the user may enter a custom cause and provide a short description for it. Based on the root-cause(s) selected by the user, a list of risk controls that mitigate the identified root-causes 320 may be provided to the user who can further select the appropriate corrective risk control actions 322.

In accordance with aspects of the present disclosure, the system 100 may be configured to identify actions and any associated objects from obtained textual input by at least identifying verbs and inferring any associated noun phrases from it via, e.g., NLP and deep neural networks.

Figure 4:
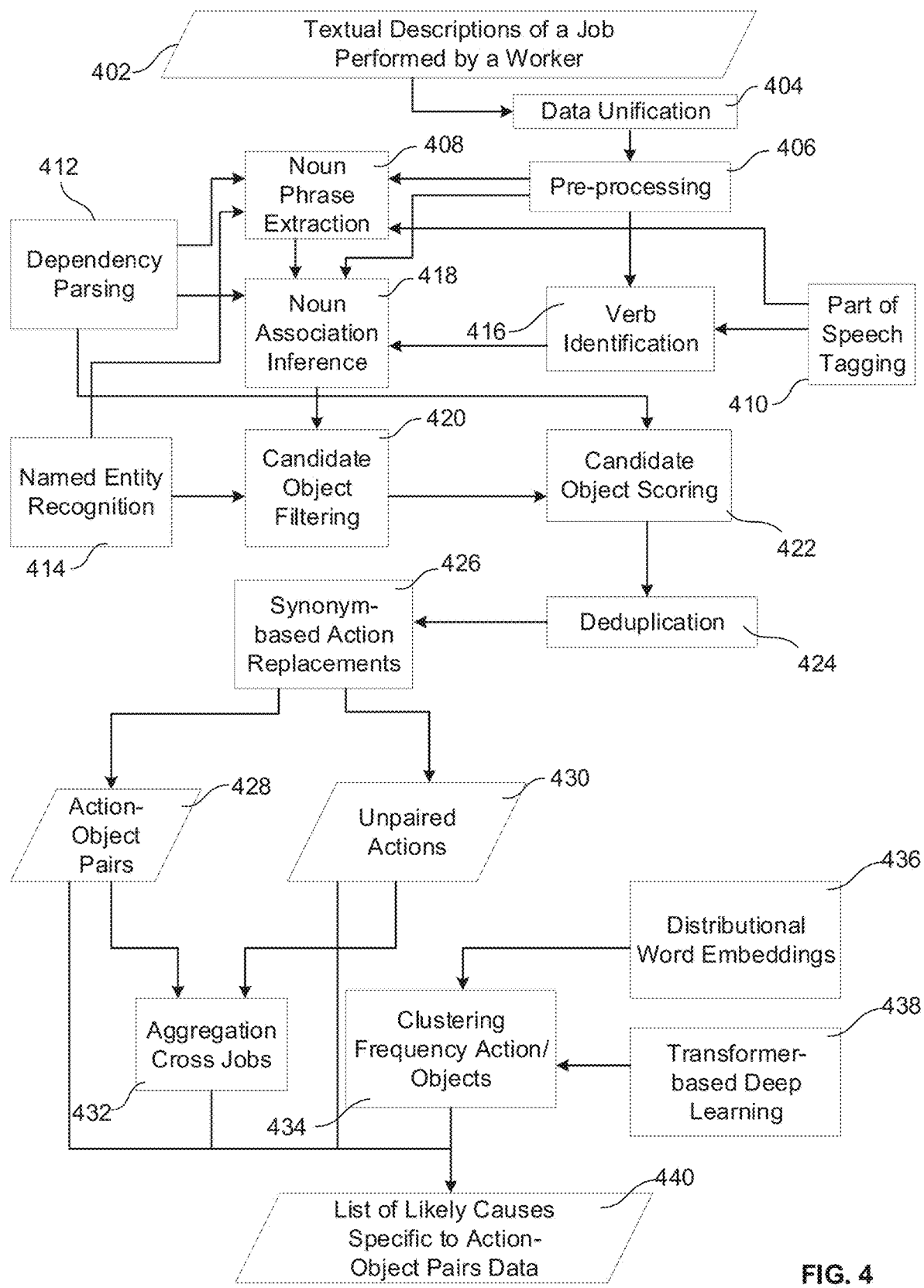
FIG. 4 illustrates a workflow of an NLP-based action-object pair inference for MSD risk root-cause identification, according to an exemplary aspect of the present disclosure.
Figure 7A:
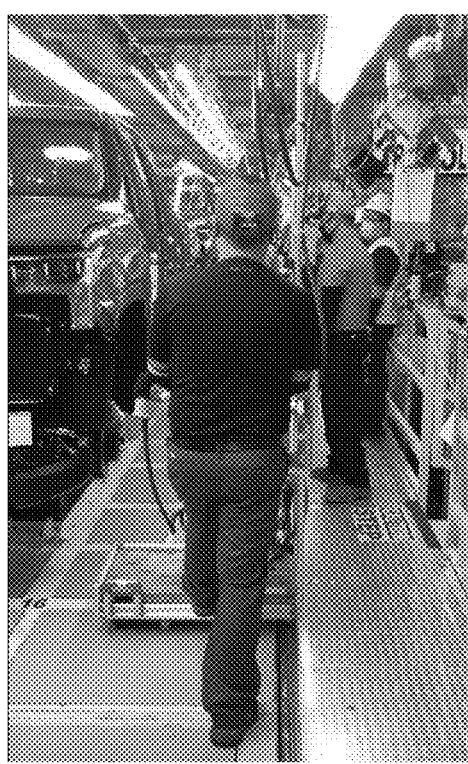
FIGS. 7(A), 7(B), 7(C) and 7(D) illustrate a number of images/frames extracted from video signals of a worker performing a first job, according to an exemplary aspect of the present disclosure.
Figure 7B:
Figure 7D:
Figure 7C:
Figure 8A:
FIGS. 8(A), 8(B), 8(C) and 8(D) illustrate a number of images/frames extracted from video signals of a worker performing a second job, according to an exemplary aspect of the present disclosure.
Figure 8B:
Figure 8D:
Figure 8C:
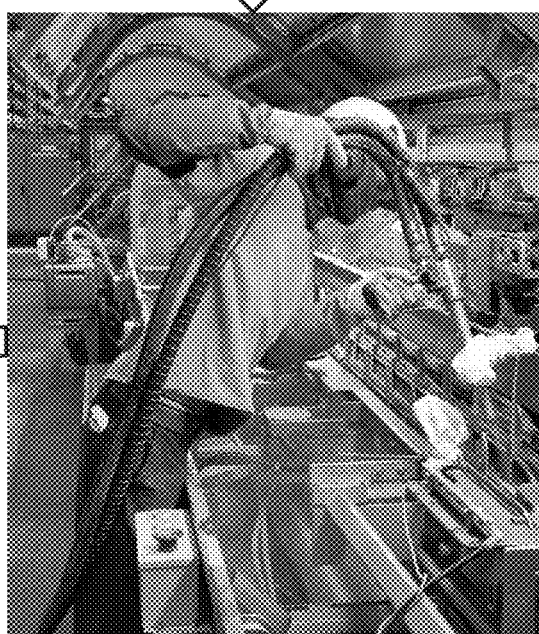
Figure 9A:
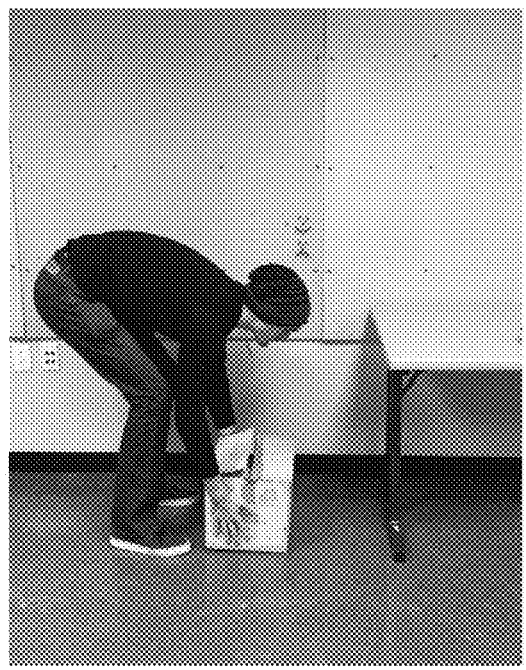
FIGS. 9(A), 9(B), 9(C) and 9(D) illustrate a number of images/frames extracted from video signals of a worker performing a third job, according to an exemplary aspect of the present disclosure.
Figure 9B:
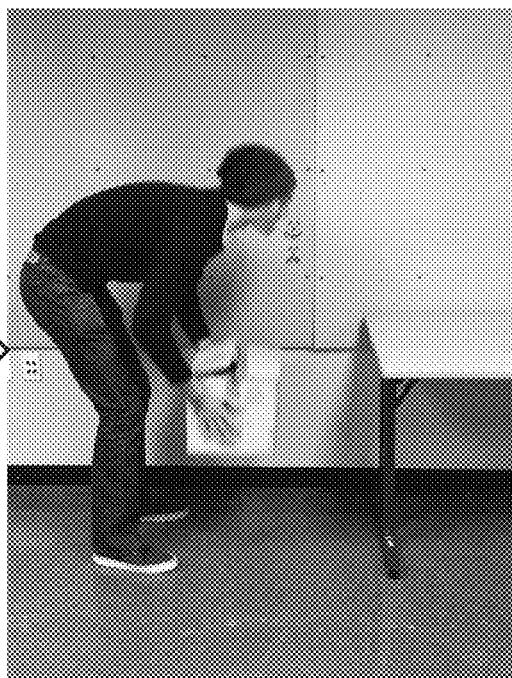
Figure 9D:
Figure 9C:
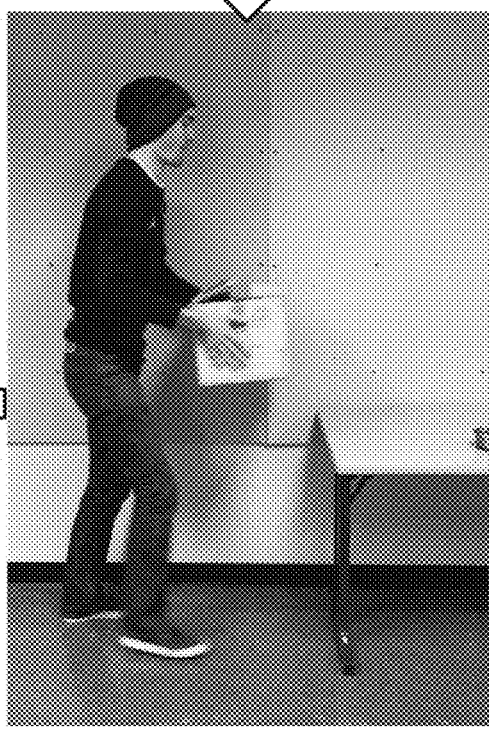
Figure 10A:
FIGS. 10(A), 10(B), 10(C) and 10(D) illustrate a number of images/frames extracted from video signals of a worker performing a fourth job, according to an exemplary aspect of the present disclosure.
Figure 10B:
Figure 10D:
Figure 10C:

Referring to FIG. 4, upon receiving textual descriptions of a job performed by a worker 402 via the user-facing application, the Cloud server system 114 of system 100 may be configured to unify 404 all relevant data to get a job-centric view of all the data through the textual input 402. For example, for each of the task data and force data shown in FIGS. 2A and 2B, the Cloud server system 114 may use columns that uniquely identify a job (job-ID columns) to group rows. Each resultant group contains information about all the forces or tasks associated with a specific job. For each group, the Cloud server system 114 may aggregate the values in each of the non-job-ID columns into a list. This process may result in one row for each group and hence each job. Each row may provide information about the forces or tasks associated with the job. Any empty or missing values may be removed from each list in each row. These steps may result in two sets of data and each row in either set of data may contain useful information about a job. The Cloud server system 114 may then perform a union of the two sets of data through an outer join 404. The resultant single piece of data may comprise a list of forces and a list of tasks for each job (row). For example, FIG. 5 shows the job-centric data resulting from the unification of the data of FIGS. 2A and 2B.

The Cloud server system 114 may then be configured to apply any suitable artificial intelligence oriented NLP techniques on the two description columns, each of which may contain lists of textual entries describing the forces or tasks associated with jobs, in the unified data. For each row, all textual entries may be collected across the two description columns and any duplicates may be removed, resulting in a single set of entries. In one aspect, NLP-based extraction and inference may be performed by the Cloud server system 114 on each textual entry in this set (hereinafter "set_all_descriptions"). Each textual entry may be pre-processed 406 by removing certain special characters and replacing certain other special characters such as "/" with words conveying similar meanings. Thereafter, in a preferred embodiment, all noun phrases in each textual entry may be identified 408 using PoS tagging 410. PoS tagging, or grammatical tagging, generally refers to the automatic assignment of part-of-speech tags to words in a sentence. A PoS is a grammatical classification that commonly includes verbs, adjectives, adverbs, nouns, etc. The Cloud server system 114 may use PoS tagging for machine translation, word sense disambiguation, and question answering parsing. In some implementations, one or more user-defined rules may be used to assign tags to words in a sentence. In the context of ergonomic risk analysis, these user-defined rules may be generated based on linguistic features of the language typically used in describing a working environment and work tasks, such as lexical, morphological, and syntactical information. Machine learning may be used to construct these rules based on an annotated corpus (textual input). In other implementations based on artificial intelligence oriented PoS tagging, machine learning or deep learning techniques may be used to determine an efficient PoS tagging model (e.g., a balanced and maximum number of tokens within a corpus) in the context of ergonomic risk analysis.

Subsequently, the phrases whose root nouns are subjects may be filtered out because such noun phrases do not constitute any objects associated with an action analyzed by the Cloud server system 114. Dependency parsing 412, which represents the grammatical structure of any textual entry via a dependency tree specifying the relationships between words in the textual entry, may be used to verify whether the root noun of a noun phrase is a subject. In addition, the Cloud server system 114 may remove the noun phrases containing any verbs, which represent actions. Single-word nouns may be included in the list of noun phrases used by the Cloud server system 114 for this filtering process. In one aspect, the Cloud server system 114 may be configured to standardize the noun phrases by reducing them to their root forms and removing determinants such as articles in order to reduce the computational cost.

Other suitable information extraction techniques may be used by the Cloud server system 114 to detect and remove noun phrases from a textual entry. For example, named entity recognition (NER) 414 may classify text from a document or corpus into some predefined categories such as person name, location name, organization name, month, date, time, etc. The Cloud server system 114 may remove certain words in response to detecting that these words are parts of named entities via NER. Regular expressions may be identified via pattern matching (e.g., explorative pattern recognition or descriptive pattern recognition) to remove noun phrases from a textual entry, because a position of a word in a sentence may be detected if the single word is an object or subject in that sentence on a syntactic level. For example, the Cloud server system 114 may use a machine learning algorithm to classify a textual input, identify, and remove the noun phrases therein based on the inherent pattern of the textual input. Further, the Cloud server system 114 may be configured to maintain a mapping from the positions of the root nouns of the noun phrases in the entry to the corresponding noun phrases.

In accordance with important aspects of the present disclosure, all verbs in a textual entry describing a series of task activities performed by a worker may be detected 416 by the Cloud server system 114 via PoS 410, similar to the aforementioned noun phrase extraction 408.

For each verb passing a pattern matching based check, the Cloud server system 114 may be configured to identify a (root) noun associated with it 418 via, e.g., dependency parsing 412. For example, in response to detecting that there is a noun associated with a verb, the Cloud server system 114 may determine three possibilities concerning the noun's position relative to the verb in a dependency tree: 1) The noun is above the verb; or 2) The noun is below the verb; or 3) The noun is a sibling of the verb. A dependency tree may generally refer to a grammatical structure of a given textual input by attaching each linguist unit to another, which will be considered its head or parent, to finally gather all these directed links into a tree-like structure. In one embodiment, the Cloud server system 114 may assume one noun per verb so as to minimize the instances of spurious detection. Specifically, in order to address possibility No. 1 (i.e., locating the noun if it is located above the verb in the dependency tree), the Cloud server system 114 may iteratively identify the parents of the verb in the dependency tree for a fixed number of times. This fixed hyperparameter, which specifies the maximum number of levels that the Cloud server system 114 traverses above the verb (or below the verb while addressing possibility No. 2), is referred to as max_path_length and may be selected experimentally. For each parent, the Cloud server system 114 may determine whether it is a suitable root noun using the position-to-noun-phrase mapping discussed above. If it is, the Cloud server system 114 may determine the noun phrase corresponding to the parent (using its position) as a candidate object and conclude the search. If it is a verb, the Cloud server system 114 may stop the search for a noun for the current verb, as any subsequent nouns that the Cloud server system 114 may encounter are closer to the parent verb and are therefore more likely to be associated with that verb.

For addressing possibility No. 2 (i.e., locating the noun if it is located below the verb in the dependency tree), the Cloud server system 114 may perform a level-order traversal of the subtree rooted at the current verb to evaluate its child nodes. For example, the Cloud server system 114 may be configured to traverse this subtree for max_path_length levels excluding the root. Such a level-order traversal may be used to evaluate the child nodes in the order of their distances to the root. For each child, the Cloud server system 114 may determine whether it is a suitable root noun as discussed above. If it is, the Cloud server system 114 may determine the noun phrase corresponding to the child (using its position) as a candidate object and conclude the search. If it is a verb, the Cloud server system 114 may stop the search for a noun for the current verb.

With respect to possibility No. 3 (i.e., locating the noun if it is a sibling of the verb in the dependency tree), the Cloud server system 114 may be configured to determine whether the parent of the verb is a verb. If that is the case, the Cloud server system 114 may stop the search, as any nouns that are siblings of the current verb are more likely to be associated with the parent. Otherwise, the Cloud server system 114 may identify the noun phrases corresponding to all siblings that are suitable root nouns (using their positions) as candidate objects.

Subsequently, the Cloud server system 114 may be configured to filter out candidate objects 420 via NER 414. Specifically, the Cloud server system 114 may remove the candidate objects whose root nouns are parts of named entities. Moreover, pattern matching may be performed to filter out candidates and replace them with the cleaned root forms of their root nouns in some cases with a view to removing noisy elements.

The Cloud server system 114 may compute and keep track of a score for each candidate object 422. Once all candidates are identified, the Cloud server system 114 may identify the candidate object with the highest score as the object, pair it with the current verb, and include the pair in the list of action-object pairs. If no noun (candidate object) is found to be associated with the current verb, the Cloud server system 114 may include the verb in the list of unpaired actions.

In one aspect, two sets of information relating to a candidate object may be used by the Cloud server system 114 for candidate object scoring 422. A first set of information may include the length of the path from the verb to the root noun of the candidate object. The smaller the length (i.e., the closer a distance between the verb and the root noun), the higher the score. The candidates stemming from the search based on the aforementioned possibility No. 3 may be given such a low score that these candidate objects cannot outscore the other candidates, because possibilities No. 1 and No. 2 are considerably more likely than possibility No. 3. With respect to a second set of information, the score of a candidate object may be based on whether the root noun is an object or not as per the dependency parsing. Nouns that are objects may be preferable. In some embodiments, the second set of information may be given less weight than the first set of information in the scoring of candidate objects.

After all verbs are detected from a textual entry and the associated objects (if any) are inferred, the Cloud server system 114 may remove any duplicates 424 from the list of unpaired actions as well as the list of action-object pairs. After all textual entries in set_all_descriptions associated with each row (and hence job) are processed, the Cloud server system 114 may combine the lists of action-object pairs inferred from all the entries and remove the duplicates, resulting in a single list of action-object pairs per row. The same steps may also be carried out on the lists of unpaired actions identified. Thereafter, the Cloud server system 114 may remove any actions in the list of unpaired actions that are found in the list of action-object pairs.

For each row shown in FIG. 5, the Cloud server system 114 may check for synonyms of the actions in the two inferred lists in the actions-of-interest list provided by ergonomists 426. For example, the Cloud server system 114 may initially determine a dense word embedding (vector) for each action in each list using pre-trained GLoVe word embeddings trained on large corpora of text aimed at preserving semantic relationships. Subsequently, the Cloud server system 114 may find its Cosine similarity (the Cosine of the angle between the two vectors to quantify how similar two elements are) with the GLoVe word embedding of each action in the actions-of-interest list. The Cloud server system 114 may determine the action in the actions-of-interest list with the best similarity value as the best potential synonym. If the similarity value of the best potential synonym exceeds a pre-defined threshold (an experimentally determined hyperparameter), the Cloud server system 114 may identify it as the actual best synonym and replace the extracted action with it. The Cloud server system 114 may also maintain a list of new actions (those with no synonyms in the actions-of-interest list) per row using both the lists. Any duplicates from the modified list of unpaired actions as well as the modified list of action-object pairs may be removed. The Cloud server system 114 may also remove any actions in the list of unpaired actions that are found in the list of action-object pairs.

Finally, the Cloud server system 114 may aggregate 432 the actions contained in the two lists (action-object pairs list 428 and unpaired actions list 430) over all rows into the list of all (unique) actions extracted across jobs. The Cloud server system 114 may also aggregate the new actions found across rows into the list of all new actions identified across jobs. Moreover, the Cloud server system 114 may populate the list of all objects identified across jobs using the list of action-object pairs per row. The Cloud server system 114 may also build the list of all action-object pairs found across jobs. For each of these four lists, the Cloud server system 114 may also calculate and report the frequency of occurrence of each item.

In another aspect, the Cloud server system 114 may perform the clustering 434 of the n most frequent actions and m most frequent objects extracted across jobs, where n and m are determined in accordance with data statistics, as follows.

Initially, a distributional word embedding technique (e.g., GloVe) 436 may be implemented to create vector representations of the actions, each of which may be a single word. To encode the objects, which may include noun phrases, the Cloud server system 114 may utilize a transformer based deep learning model (e.g., DistilBERT) 438 aimed at language understanding to generate dense, contextual embeddings. The Cloud server system 114 may use the final-layer hidden state for the CLS token from the DistilBERT tokenization as the text embedding. The Cloud server system 114 may explore multiple clustering approaches for clustering 434 the actions/objects based on their vector representations including K-Means and DBSCAN. The Cloud server system 114 may also experiment with multiple distance metrics, namely the Euclidean distance and Cosine distance (derived from Cosine similarity). While K-Means inherently uses the Euclidean distance, the Cloud server system 114 may apply DBSCAN using the Cosine distance. The Cloud server system 114 may also develop and experiment with clustering techniques based on thresholding pairwise Cosine distances using e.g., a greedy approach. In another embodiment, a point may be assigned to an existing cluster if any of the cluster members is within an experimentally tuned distance threshold of it and a new cluster otherwise. If the point is found to be close to multiple clusters, they are all merged. Based on the job-wise information extracted pertaining to actions and objects as well as the overall information, the Cloud server system 114 may efficiently identify 440 a list of likely root-causes of WMSD risks at a workplace. For example, referring to FIG. 6, the Cloud server system 114 may be configured to automatically identify action-object pairs 606 and unpaired actions 608 based at least upon obtained textual information (e.g., user descriptions of tasks associated with a job if any 604 and/or user descriptions of forces associated with a job if any 602) for each of 10 different jobs.

The following four examples will further illustrate how system 100 of the present disclosure may be configured to identify the most likely root-causes of high ergonomics risks at a workplace based at least upon video signals of a worker performing a job and textual information describing a series of work activities of the job and/or forces being exerted during these work activities and provide recommended corrective risk control actions accordingly.

Referring to FIGS. 7(A)-7(D) (Example 1), a user (e.g., one of 102a, 102b . . . 102n of FIG. 1) may upload a video of a worker performing a first job via the application installed on one of the computing devices 104, 106 or 108. The application may prompt the user to enter textual information regarding specific task activities being performed and force being exerted. For example, as shown in FIG. 11, the user may describe that the worker is performing assembling and joining parts (user provided descriptions of tasks performed 1104), and the forces exerted 1102 including moving cart, sticking a strip, drilling holes, and tightening screws. Subsequently, the Cloud server system 114 may be configured to process received video signals and textual information to extract images/frames respectively showing the worker moving a cart (FIG. 7(A)), sticking a strip (FIG. 7(B)), drilling holes (FIG. 7(C)), and tightening screws (FIG. 7(D)). As shown in FIG. 12, the Cloud server system 114 may be configured to identify action-objects pairs 1202 (e.g., (move, cart), (stick, strip), (tighten, screw), (join, part)) and unpaired actions 1204 (e.g., assemble) of Example 1 based upon the obtained textual inputs, as described above with respect to FIG. 4.

Referring now to FIGS. 8(A)-8(D) (Example 2), a user (e.g., one of 102a, 102b . . . 102n of FIG. 1) may upload a video of a worker performing a second job via the application installed on one of the computing devices 104, 106 or 108. The application may prompt the user to enter textual information regarding specific task activities being performed and force being exerted. For example, as shown in FIG. 11, the user may describe that the worker is washing mechanical parts (user provided descriptions of tasks performed 1104), and the forces exerted 1102 including operating a hose. Subsequently, the Cloud server system 114 may be configured to process received video signals and textual information to extract images/frames showing the worker operating a hose to wash various mechanical parts. As shown in FIG. 12, the Cloud server system 114 may be configured to identify action-objects pairs 1202 (e.g., (operate, hose), (wash, mechanical parts)) of Example 2 based upon the obtained textual inputs, as described above with respect to FIG. 4.

Referring now to FIGS. 9(A)-9(D) (Example 3), a user (e.g., one of 102a, 102b . . . 102n of FIG. 1) may upload a video of a worker performing a third job via the application installed on one of the computing devices 104, 106 or 108. The application may prompt the user to enter textual information regarding specific task activities being performed and force being exerted. For example, as shown in FIG. 11, the user may describe that the worker is lifting a box (user provided descriptions of tasks performed 1104), and the forces exerted 1102 including lifting the box. Subsequently, the Cloud server system 114 may be configured to process received video signals and textual information to extract images/frames showing the worker lifting a box. As shown in FIG. 12, the Cloud server system 114 may be configured to identify action-objects pairs 1202 (e.g., (lift, box)) of Example 3 based upon the obtained textual inputs, as described above with respect to FIG. 4.

Referring now to FIGS. 10(A)-10(D) (Example 4), a user (e.g., one of 102a, 102b 102n of FIG. 1) may upload a video of a worker performing a fourth job via the application installed on one of the computing devices 104, 106 or 108. The application may prompt the user to enter textual information regarding specific task activities being performed and force being exerted. For example, as shown in FIG. 11, the user may describe that the worker is attaching a part (user provided descriptions of tasks performed 1104), and the forces exerted 1102 including moving a part and turning an object. Subsequently, the Cloud server system 114 may be configured to process received video signals and textual information to extract images/frames showing the worker moving a part to a workstation and turning an object to attach to the part. As shown in FIG. 12, the Cloud server system 114 may be configured to identify action-objects pairs 1202 (e.g., (move, part), (turn, object), (attach, part)) of Example 4 based upon the obtained textual inputs, as described above with respect to FIG. 4.

In one aspect, the Cloud server system 114 may be configured to determine clusters from identified actions and objects across various jobs. With respect to Examples 1-4 discussed above, FIG. 13 illustrates action clusters inferred across the four jobs (e.g., push, stick tighten, operate, turn, attach, assemble, join, wash, lift) and object clusters inferred across the four jobs (e.g., screw, hose, box, mechanical part, object, part, cart, strip) by the Cloud server system 114.

As described above with respect to FIG. 3, system 100 of the present disclosure may be configured to utilize computer vision technology and deep learning framework to process the uploaded video signals and generate estimates for various body joint locations, determine primary risk exposure type (e.g., posture or force) 312, and identify body region(s) with WMSD risk exposure 314. For example, the user-facing application of the system 100 may include a plurality of modules executed and controlled by the processor of the hosting computing device or system 104, 106 or 108 for obtaining, analyzing and processing a video. In one embodiment, a video receiving/communication interface module (not shown) of the user-facing application may prompt the user of the system 100 to directly record a video of a worker performing a series of work activities via the hosting computing device or system 104, 106 or 108. In another embodiment, the video receiving/communication interface module may be configured to receive video signals via, e.g., a universal serial bus (USB) connector (e.g., USB-A, USB-B, USB-B Mini, USB-B Micro, USB-C, USB4, Lightning) or any suitable ports or connectors, from external sources (e.g., any suitable video file storage devices or video players such as CD/DVD disc players, digital cameras and sensors, web cameras, or any suitable computing devices and imaging devices with video recording capabilities). In some embodiments, the video receiving/communication interface module may be configured to receive video transmission signals in both analog and digital formats. Further, the user-facing application may use a control module (e.g., processor/microprocessor of the hosting computing device or system 104, 106 or 108) to identify the file format of the received video and determine whether the video is eligible for motion capture processing (e.g., 2D joint location prediction). In certain embodiments, a video format converting module (not shown) may be implemented for converting the format of video signals originally received by the video receiving interface module into digital video files in a targeted format required by the Cloud server system 114 for further processing. The system 100 of the present disclosure may process and convert video files in various formats including but not limited to MP4 (MPEG-4 Part 14), MOV (QuickTime Movie), WMV (Windows Media Viewer), AVI (Audio Video Interleave), AVCHD (Advanced Video Coding High Definition), flash video formats FLV, F4V, and SWF (Shockwave Flash), MKV, WEBM or HTML5, and MPEG-2. Subsequently, the video receiving/communication interface module may transmit the obtained video signals to the Cloud server system 114 or any of external data services 116a, 116b, 116c, . . . 116n for an initial verification whether the video is eligible for motion capture processing (e.g., 2D joint location prediction) and/or format conversion. For example, a number of parameters may be checked during the initial verification process: the resolution of the video recording; the bitrate of the vedio recording; the duration of the video recording; the file size of the video recording; and the format of the video recording. In a preferred embodiment, video files in MP4 or MOV format may be used by the Cloud server system 114.

To facilitate bi-directional communication, the video receiving/communication interface module of the user-facing application may also be used to receive the stream of video signals transmitted from one or more multimedia data processing sources (e.g., the Cloud server system 114 or any of external data services 116a, 116b, 116c, . . . 116n), save the received video signals locally on the hosting computing device or system 104, 106 or 108, and/or transmit the received video signals to other computing devices deployed within the system 100.

The uploaded video may be transmitted to the Cloud server system 114 for processing. For example, the video may be disassembled into image frames using a rate of 30 fps. Each image frame generated in the previous step may be processed using a deep learning model to estimate the 2D keypoint (joint locations) estimation for the worker in the image.

For example, after localizing and segmenting the subject (e.g., the worker performing the job) in the video sequence, the Cloud server system 114 may be configured to take a color image of size w×h as the input and generate the 2D locations of anatomical keypoints for each person in the image as the output. The input may include at least one of an image, video files, and information provided by webcam, Flir/Point Grey, IP camera, or any custom input source (e.g., depth camera). The output may include basic image optionally overlayed with keypoints and saving (PNG, JPG, AVI, . . . ), keypoint saving (JSON, XML, YML, . . . ), keypoints as array class, and custom output code (e.g., certain fancy UI).

A skeleton structure of a human body (human torso and head and limb position diagram of the body) generated by computer vision and motion capture technology of the present disclosure may determine the geometric structure of the human movement. Relative position of the joints in the skeleton may determine the posture of the body. Skeleton estimation may be performed based on depth images or RGB images that may be obtained from pictures or video recordings.

A depth image usually contains the position information of an object identified in the image (e.g., human joint points). Therefore, human skeletons may be estimated based on the position information of joint points to infer human behavior. There are two methods to obtain depth images: passive range sensor and active depth sensor. For example, the most commonly used method of the passive range sensor is binocular stereo vision, which obtains two images of the same scene at the same time by two cameras with a certain distance apart, locates the corresponding pixel points in two images by stereo algorithm, and then calculates the time difference information according to the triangle principle. The time difference information can represent the depth information of the object in the scene by conversion. Based on the stereo matching algorithm, the depth image of the same scene can also be obtained by photographing a group of images with different angles in the same scene. Compared with the passive range sensor, the active depth sensor has the most important feature: the equipment itself needs to transmit energy to complete the depth information collection. Example active depth sensors may include time-of-flight cameras and Kinect sensors.

RGB images based skeleton estimation includes human skeleton keypoints detection. It mainly detects certain keypoints of a human body, and determines human skeleton information through these keypoints.

In one embodiment, the Cloud server system 114 may be configured to receive use RGB images (e.g., image frames obtained from the received video signals) as an input and process them through a baseline convolutional neural network (CNN) to extract the feature maps in the input. Each feature map is then processed in a multi-stage CNN pipeline to generate confidence maps of different body part locations such as the neck, right shoulder, right elbow, and right knee. At the same time, a degree of association among different body parts may be determined. In one embodiment, at the first stage of the deep learning, the Cloud server system 114 may be configured to generate an initial set of detection confidence maps and a set of representations of unstructured pairwise relationships among body parts. In each subsequent stage of the deep learning processing, the predictions in the previous stage along with the original image features may be concatenated by the Cloud server system 114 and used to generate more refined predictions of various body parts. As the stage progresses, the initial confusion between different body parts may be resolved and the Cloud server system 114 may be configured to distinguish different body parts more accurately. The final confidence maps and body part relationship determination may then passed into an inference algorithm (e.g., greedy algorithm) for further optimization. Loss functions may be implemented to minimize the error between the predicted and target outputs.

The estimated 2D joint locations for all the body joints may not be accurate for all the frames, as some of these joints may suffer from occlusion due to obstruction from other body parts or other objects. Therefore, the Cloud server system 114 may be configured to perform post processing steps to recover occluded joint locations. In one aspect, for each estimated joint location, the Cloud server system 114 may be configured to detect the frames, where the joint has a low confidence value (likely due to occlusion). In those detected frames, the Cloud server system 114 may interpolate the position of the occluded joint over time based on its angle and distance from its parent joint. For example, a left elbow joint and a left wrist joint of one individual in an image frame are parent-child joints for a specific limb. In some embodiments, a parent-child joint relationship may represent a kinematic and dynamic relationship between two adjacent and connected body joints. A parent joint may refer to a body joint that constrains the degrees of freedom between the parent and child joints.

After post processing of the estimated joint locations, joint angles for certain body regions (e.g., neck, back, hand/wrist, left shoulder, right shoulder, left elbow, right elbow, left knee and right knee) may be calculated by the Cloud server system 114 using the respective joint location estimations.

In one aspect, the Cloud server system 114 may be configured to perform the MSD risk evaluation (calculation of priority risk scores). For example, a MSD risk evaluation may output specific information about a number of body regions, such as shoulder, elbow, or back, with MSD risk scores and the type (posture or force) of each risk exposure. Posture information may indicate the angle that occurs at the joint. These risk scores may be calculated using the joint angle information estimated form the user uploaded video, and force information entered by the user.

In one aspect, the Cloud server system 114 may be configured to perform the MSD risk evaluation (calculation of priority risk scores). For example, a MSD risk evaluation may output specific information about a number of body regions, such as shoulder, elbow, or back, with MSD risk scores and the type (posture, duration, frequency, or force) of each risk exposure. These risk scores may be calculated using the joint angle information estimated form the user uploaded video, and optional force information entered by the user.

In one embodiment, in order for the Cloud server system 114 to calculate the risk scores, the joint angles may be compared with respective threshold values to calculate a risk score for each of a plurality of body regions of the worker in each of a plurality of risk categories (e.g., awkward postures, their duration and frequency during the job task). Based upon these individual risk scores, overall risk rating for a specific body region may be calculated. In one embodiment, the overall risk rating may finally be categorized as force risk or posture risk.

As will be described fully below, a priority risk score may be calculated for risk category "Awkward Postures," in accordance with aspects of the present disclosure. Postural risk scores may be determined based on the range of motion for a body joint. Postures that are nearer the extremes of the range of motion are scored as higher risk, while those closer to neutral posture have a lower (or zero) score. Specifically, the Cloud server system 114 may calculate a risk score for each body region (including left and right sides for the upper limbs) for a worker's postures between 0 (no effect) and 3 (highest risk), based on the worst posture that has been identified from the video for that body region.

It is known that human wrist generally acts as a bridge between the hand and the forearm and it is capable of many diverse movements and positions. The neutral position for a wrist typically refers to a position where no major forearm muscles are engaged to maintain a posture. Wrist flexion is the downward bending of the wrist. Wrist extension refers to bending the wrist backwards towards the posterior section of the forearm. Ulnar deviation of the wrist refers to the pivoting of the wrist towards the little finger or ulnar bone. It is also referred to as ulnar flexion. The opposite of ulnar, radial deviation of the wrist points to the bending of the wrist towards the thumb or radial bone, which is also referred to as radial flexion. In one embodiment, the Cloud server system 114 may compare the joint angles of a worker's hand/wrist calculated based on the uploaded video with a number of selected threshold values to determine a risk rating.

In one embodiment, in response to detecting that the hand/wrist flexion angle ≥20 degrees, extension angle ≥20 degrees, ulnar flexion angle ≥10 degrees, and radial angle ≥10 degrees in an awkward posture, the Cloud server system 114 may assign 1 point for this specific body part. Further, in response to detecting that the hand/wrist flexion angle ≥40 degrees, extension angle ≥40 degrees, ulnar flexion angle ≥20 degrees, and radial angle ≥20 degrees, the Cloud server system 114 may assign 2 points. The highest risk score 3 may be assigned if the hand/wrist flexion angle ≥60 degrees, extension angle ≥60 degrees, ulnar flexion angle ≥30 degrees, and radial angle ≥30 degrees.

In certain embodiments of the present disclosure, elbow posture may be only scored when the worker's shoulder angle is detected to be ≥60 degrees. For example, the Cloud server system 114 may respectively assign 1 point for a detected elbow angle that is between 90 and 119 degrees, 2 points for the range of 120-149 degrees, and highest risk score 3 if the elbow angle is detected to be in the range of 150-180 degrees.

In yet another embodiment, in response to detecting that the shoulder angle ranges between 45 degrees and 89 degrees in a posture, the Cloud server system 114 may assign 1 point for this specific body region. In response to detecting that the shoulder angle is in the range of 90-119 degrees or 0-(−19) degrees, the Cloud server system 114 may assign 2 points. The highest risk score 3 may be assigned if the shoulder angle is detected to be ≥120 degrees, or ≥(−20) degrees.

The neck, also called the cervical spine, is a well-engineered structure of bones, nerves, muscles, ligaments, and tendons. The cervical spine has 7 stacked bones called vertebrae, allowing the neck to move in all directions. For example, the cervical spine can bend directly forward with the chin tilting down. Neck flexion typically occurs when looking downward or while in forward head posture. Neck extension typically occurs when the cervical spine straightens or moves directly backward with the chin tilting up. Neck rotational movement or twist allows the head to turn to one side. Lateral flexion of the cervical spine occurs when the head bends to one side with the ear moving toward the shoulder. In accordance with aspects of the present disclosure, in response to detecting that the forward bend angle is between 140-159 degrees, twist angle ≥20 degrees, or lateral bend angle ≥15 degrees, the Cloud server system 114 may assign 1 point to the posture for this specific body region. Moreover, in response to detecting that the forward bend angle is between 120-139 degrees or backward bend angle is between 0-(−19) degrees, or twist angle >40 degrees, or lateral bend angle >30 degrees, 2 points may be assigned.

The highest risk score 3 may be assigned if the forward bend angle ≤119 degrees or backward bend angle ≥(−20) degrees, or twist angle >60 degrees, or lateral bend angle >45 degrees.

The spine or back movements of a person generally include flexion, extension, rotation and lateral flexion, similar to the neck movements described above. These movements occur as a combination of rotation and translation in the sagittal, coronal and horizontal planes. In accordance with aspects of the present disclosure, in response to detecting that the forward bend angle of the back is between 120-149 degrees, twist angle >20 degrees, or lateral bend angle >15 degrees, the Cloud server system 114 may assign 1 point to the posture for this specific body region. Moreover, in response to detecting that the forward bend angle is between 90-119 degrees or backward bend angle is between 0-(−19) degrees, or twist angle >45 degrees, or lateral bend angle >30 degrees, 2 points may be assigned. The highest risk score 3 may be assigned if the forward bend angle ≤89 degrees or backward bend angle ≥(−20) degrees, or twist angle >90 degrees, or lateral bend angle >45 degrees.

In some implementations, the uploaded video of the present disclosure may capture the left-side or right-side sagittal plane views of an operator performing a job. As a result, the Cloud server system 114 may be configured to determine knee angles based upon the perspective of the obtained video recording and compare the knee angles with a number of threshold values. For example, in response to detecting that the knee angle (left or right side) is in the range of 120-149 degrees, the Cloud server system 114 may assign 1 point to the posture for this specific body part. If the knee angle is detected to be between 90-119 degrees, the Cloud server system 114 may assign 2 points. The highest risk score 3 may be assigned if the knee angles is ≤89 degrees.

Generally, ergonomic risk factors act in combination to create a hazard at the workplace. Work tasks that have multiple risk factors have a greater likelihood of causing a WMSD, depending on the duration, frequency, and magnitude of exposure to each. Thus, it is important that ergonomic risk factors be considered in light of their combined effect in causing or contributing to a WMSD.

For example, maintaining the same work positions or postures for a long period of time may increase the amount of force required to do a task because, in addition to the force required to perform the task, contraction forces must be applied to hold the body in position throughout the work shift. Maintaining the same position or posture may require holding the arms and shoulders in a non-neutral posture without moving. The effects of maintaining the same work positions can occur in almost any joint of the body and vary depending on body location. A priority risk score may be calculated for risk category "Duration," in accordance with aspects of the present disclosure.

In an embodiment, the Cloud server system 114 may be configured to identify the worst postures of a work task (e.g., two or worst postures) with risk scores of 1, 2 or 3 from the frame-by-frame analysis of the uploaded video recording and determine the percent of time of one or more body regions in the identified postures. If a body region is involved in the job task between 10-19% of the time in the identified postures, the Cloud server system 114 may assign 1 point to that body region, 2 points if the percent of time is between 20-29% of the time, and 3 points if the percent of time is greater or equal to 30%.

Moreover, a priority risk score may be calculated for risk category "Frequency," in accordance with aspects of the present disclosure. Specifically, the Cloud server system 114 may calculate a score for each body region (including left and right sides for the upper limbs) for a worker's postures between 0 (no effect) and 1, based on the frequency of occurrence during a selected period of time calculated from the video for that body region.

In one embodiment, the Cloud server system 114 may be configured to identify hand/wrist movements in any combination postures scored 1 or higher during a selected period of time (e.g., one minute or any suitable time interval). The Cloud server system 114 may assign 1 point to this body region (hand/wrist) in response to detecting more than 30 such occurrences. For all other body regions, the Cloud server system 114 may assign 1 point in response to detecting more than 3 such occurrences.

Performing forceful exertions requires an application of considerable contraction forces by the body of a worker, which causes muscle fatigue rapidly. Excessive or prolonged exposure to forceful exertions may lead to overuse of muscles and may result in muscle strain, soreness and damage. Performing forceful exertions may also irritate tendons, joints and discs, which may cause inflammation, fluid build-up, and constriction of blood vessels and nerves. Increased compression of nerves from the pressure imposed by inflamed tendons or muscle contractions may cause disorders of the nervous system (carpal tunnel syndrome and other nerve entrapment disorders).

Injuries related to forceful exertions can occur in any tissue or joint. Lifting/lowering, pushing/pulling, and carrying heavy objects are usually the tasks that come to mind as examples of forceful lifting tasks, but high forces are also involved in other types of jobs. These may include jobs that require employees to apply pinch forces with their fingers (picking up or placing small items on an assembly line with the fingers), static forces (applying significant physical effort to put the last turn on a screw, pulling hard on a wrench to loosen a bolt), and dynamic forces (tossing objects into containers).

A priority risk score may be calculated for risk category "High Forces," in accordance with aspects of the present disclosure. Specifically, the Cloud server system 114 may calculate a risk score for each body region (including left and right sides for the upper limbs) in relation to the force applied during a job task between 0 (no effect) and 4 (highest risk), based on the obtained force information. In an embodiment, a plurality of force thresholds may be determined based on a maximum force allowed in the force direction being evaluated. The lower the percentage of the maximum force exerted by the worker, the lower the risk score.

In an embodiment, the Cloud server system 114 may calculate a score based on the force required by a job task on a worker's hand/wrist. In general, an object may be grasped using one of two methods: a pinch grip or a power grip. A power grip curls the fingers toward the palm; a pinch grip presses the thumb against the fingers of the hand or an object, and does not involve the palm. The amount of force that can be generated depends on the type of grip and the width of the grip. The Cloud server system 114 may assign 1 point if the pinch grip force applied is ≥3 lb, and/or the finger press force is ≥3 lb, and/or the power grip force is ≥13 lb. The Cloud server system 114 may assign 2 points if the pinch grip force applied is ≥5 lb, and/or the finger press force is ≥5 lb, and/or the power grip force is ≥19 lb. The Cloud server system 114 may assign 3 points if the pinch grip force applied is ≥8 lb, and/or the finger press force is ≥9 lb, and/or the power grip force is ≥32 lb. The Cloud server system 114 may assign 4 points if the pinch grip force applied is ≥10 lb, and/or the finger press force is ≥11 lb, and/or the power grip force is ≥41 lb.

For all other body regions, as disclosed previously, the user of the system 100 may provide force information including the force direction and magnitude. The Cloud server system 114 may calculate a score based on the obtained force information. For example, the Cloud server system 114 may assign 1 point to elbow/shoulder movement in a posture in a unilateral direction if the press down force is ≥6 lb, or exerted lifting/lowering force is ≥4 lb, or pull across force is ≥3 lb, or push out force (shoulder movement) ≥7 lb, or pull in force (elbow movement) ≥7 lb, or pull down force ≥9 lb. For another example, the Cloud server system 114 may assign 2 points to elbow/shoulder movement in a posture in a unilateral direction if the press down force is ≥10 lb, or exerted lifting/lowering force is ≥6 lb, or pull across force is ≥5 lb, or push out force (shoulder movement) ≥10 lb, or pull in force (elbow movement) ≥11 lb, or pull down force ≥13 lb. Further, the Cloud server system 114 may assign 3 points to elbow/shoulder movement in a posture in a unilateral direction if the press down force is ≥15 lb, or exerted lifting/lowering force is ≥10 lb, or pull across force is ≥8 lb, or push out force (shoulder movement) ≥17 lb, or pull in force (elbow movement) ≥19 lb, or pull down force ≥22 lb. The highest score 4 may be assigned to elbow/shoulder movement in a posture in a unilateral direction if the press down force is ≥21 lb, or exerted lifting/lowering force is ≥12 lb, or pull across force is ≥11 lb, or push out force (shoulder movement) ≥22 lb, or pull in force (elbow movement) ≥24 lb, or pull down force ≥29 lb.

Personal protective equipment (PPE) is a key part of managing health and safety within a variety of industrial workplaces. PPE may include any equipment that is issued to an individual for protection against risks at a workplace (e.g., hard hats, googles, gloves, overalls, trousers, and ear defenders). In accordance with aspects of the present disclosure, the Cloud server system 114 may be configured to obtain PPE information relating to the series of work activities recorded in the uploaded video, and determine a risk score accordingly. For example, when analyzing PPE-associated headache disorder or neck strain or pain as a consequence of wearing of hard hats, protective respirators, face masks or eyewear, the Cloud server system 114 may assign 1 point if the PPE weights ≥2 lb, 2 points if the PPE weights ≥4 lb, 3 points if the PPE weights ≥8 lb, and 4 points if the PPE weights ≥16 lb.

Evidence shows that work requiring stooped or squatting postures is closely associated with high incidence of lower back disorders. The squat lifting movement may be defined as flexing the knees and keeping the back as straight as possible (i.e., no forward flexion in the spine), while the stoop lifting movement is mainly achieved by a forward flexion of the spine without bending the knees. In accordance with aspects of the present disclosure, the Cloud server system 114 may perform an object lifting movement evaluation involving stoop or squat movements and/or whole-body movements. For example, the Cloud server system 114 may be configured to assign 1 point if a posture (stoop or squat) relating to a lifting/lowering movement with 2 hands of a worker and a required force ≥25 lb, or a whole-body pull/pull movement with 2 hands of a worker and a required force ≥50 lb. The Cloud server system 114 may be configured to assign 2 points if a posture (stoop or squat) relating to a lifting/lowering movement with 2 hands of a worker and a required force ≥33 lb, or a whole-body pull/pull movement with 2 hands of a worker and a required force ≥57 lb. The Cloud server system 114 may be configured to assign 3 points if a posture (stoop or squat) relating to a lifting/lowering movement with 2 hands of a worker and a required force ≥42 lb, or a whole-body pull/pull movement with 2 hands of a worker and a required force ≥64 lb. The Cloud server system 114 may be configured to assign 4 points if a posture (stoop or squat) relating to a lifting/lowering movement with 2 hands of a worker and a required force ≥50 lb, or a whole-body pull/pull movement with 2 hands of a worker and a required force ≥71 lb.

In yet another embodiment, the Cloud server system 114 may be configured to assess high forces impact on the legs/knees of a worker. For example, the Cloud server system 114 may be configured to assign 1-4 points in response to detecting that a squatting posture during a lifting/lowering movement with 2 hands of a worker and a required force ≥25 lb, ≥33 lb, ≥42 lb or ≥50 lb, respectively.

In sum, the higher the risk score for a joint or a body region, the higher the priority to assess the direct ergonomic risk causes and provide control recommendations related to the risk for the specific body region. The Cloud server system 114 of the present disclosure may be configured to calculate risk scores in 4 risk categories ("Awkward Posture," "Duration," "Frequency," and "Forces") for each identified body region and generate a composite score ranging from 0 to 11 for each body region by summing individual scores in each risk category. These body region scores may then be summed to create an overall job score ranging from 0 to 100, with one additional point being added to account for the presence of vibration at the workplace.

After the calculation of priority risk scores, the user-facing application of the system 100 may display risk scores and ratings for all identified body regions. The user may mark specific force and/or posture for each body region or multiple body regions on the application interface module to address and analyze the direct cause. Combined with the NLP-based determination of action-object pairs inferred from the textual inputs describing the work activities being performed and forces exerted, for each body region, the Cloud server system 114 of the system 100 may be configured to generate a list of potential causes and additional causes for higher risk that is specific to the body region, types of risk exposure, and action-object pairs. From the list of potential causes, the user may be prompted to select the cause that most accurately addresses the force or posture issue. Alternatively, if none of the causes from the list applies, the user may enter a custom cause and provide a short description for it.

In response to the root-cause(s) selected by the user, the system 100 may generate a list of suggested controls that may be implemented to reduce the risk for this body region. From the list of suggested controls, the user may be prompted to select improvements that may be applied. The user may also add custom improvements.

Figures 14A, 14B, 14C, 14D:
FIGS. 14(A), 14(B), 14(C) and 14(D) illustrate ergonomics risk root-cause identification results of a first example job based at least upon video signals of a worker performing the first job related to the extracted images/frames of FIGS. 7(A)-7(D) and textual information describing a series of work activities of the job and forces being exerted during these work activities, according to an exemplary aspect of the present disclosure.

Referring to FIGS. 14(A)-14(D), the user-facing application of the system 100 may display WMSD risk root-cause analysis results by the Cloud server system 114 based at least upon video signals of a worker performing the first job related to the extracted images/frames of FIGS. 7(A)-7(D) and textual information describing a series of work activities of the job and forces being exerted during these work activities. Specifically, FIG. 14(A) illustrates the WMSD risk root-cause analysis results in a number of risk categories (e.g., "Force," "Posture," "Duration," and "Frequency") for all identified body regions (e.g., neck, back, hand/wrist, left shoulder, right shoulder, left elbow, right elbow, left knee and right knee). For each body region, a numerical risk score and the total risk rating (e.g., "Lower Risk," "High Risk," and "Higher Risk") may be calculated and displayed. The user may select specific force and/or posture for each body region or multiple body regions on the application interface module to address and analyze the direct root-causes. FIG. 14(B) displays a body region selection page for detailed root-cause analysis and control suggestions. With respect to the first job (e.g., FIGS. 7(A)-7(D)), body regions that have been identified to have high or higher ergonomic risks may be further selected for direct root-cause analysis in the primary risk exposure types "Force" and "Posture." For example, in response to detecting that the user has selected "Posture Risk" analysis for the "Right Shoulder" region, one or more the direct root-causes (Level 1) may be displayed in FIG. 14(C): Bench/table/fixture is too high; Bench/table/fixture is too low; Cart grip is too low. In some embodiments, more detailed direct root-causes (Level 2) may be generated for a selected Level 1 root-cause. For example, in response to detecting that the user selects "Cart grip is too low" as one of the identified root-causes for ergonomic risks associated with the first job of FIGS. 7(A)-7(D), FIG. 14(C) shows additional attributing factors such as "Cart has no handles," "Handle is too low," or "Other" causes defined by the user. As shown in FIG. 14(D), the user may further categorize the selected root-causes (e.g., "Product Design," "Process Flow/Design," or "Equipment/Tool Design") in order to determine control suggestions. FIGS. 15(A) and 15(B) display the control suggestions and improvements to address the selected root-causes. For example, as shown in FIG. 15(A), in response to the identified Level 1 and Level 2 root-causes that "Cart grip is too low" and "Handle is too low" in the "Equipment/Tool Design" category, the Cloud server system 114 of the system 100 may be configured to generate a number of suggested controls including "Install a vertical handle," "Provide cart with optimal handle heights," "Raise handle," or any suitable "Custom Control." For each user-selected ergonomic improvement, FIG. 15(B) illustrates a number of important aspects and considerations for facilitating and managing the implementation of the improvement such as responsible personnel, cost, return on investment (ROI), control, priority, targeted date and status. The user may also add custom improvements. In one embodiment, additional information (e.g., information collected from various data sources or services 116a, 116b, 116c, . . . 116n of FIG. 1) may be presented to the user for providing or optimizing recommendations that may include text, audio, video, and other rich media explanations (e.g., a link to "Design Guidelines for Ergonomics" in FIG. 15(B)).

Figures 16A, 16B, 16C, 16D:
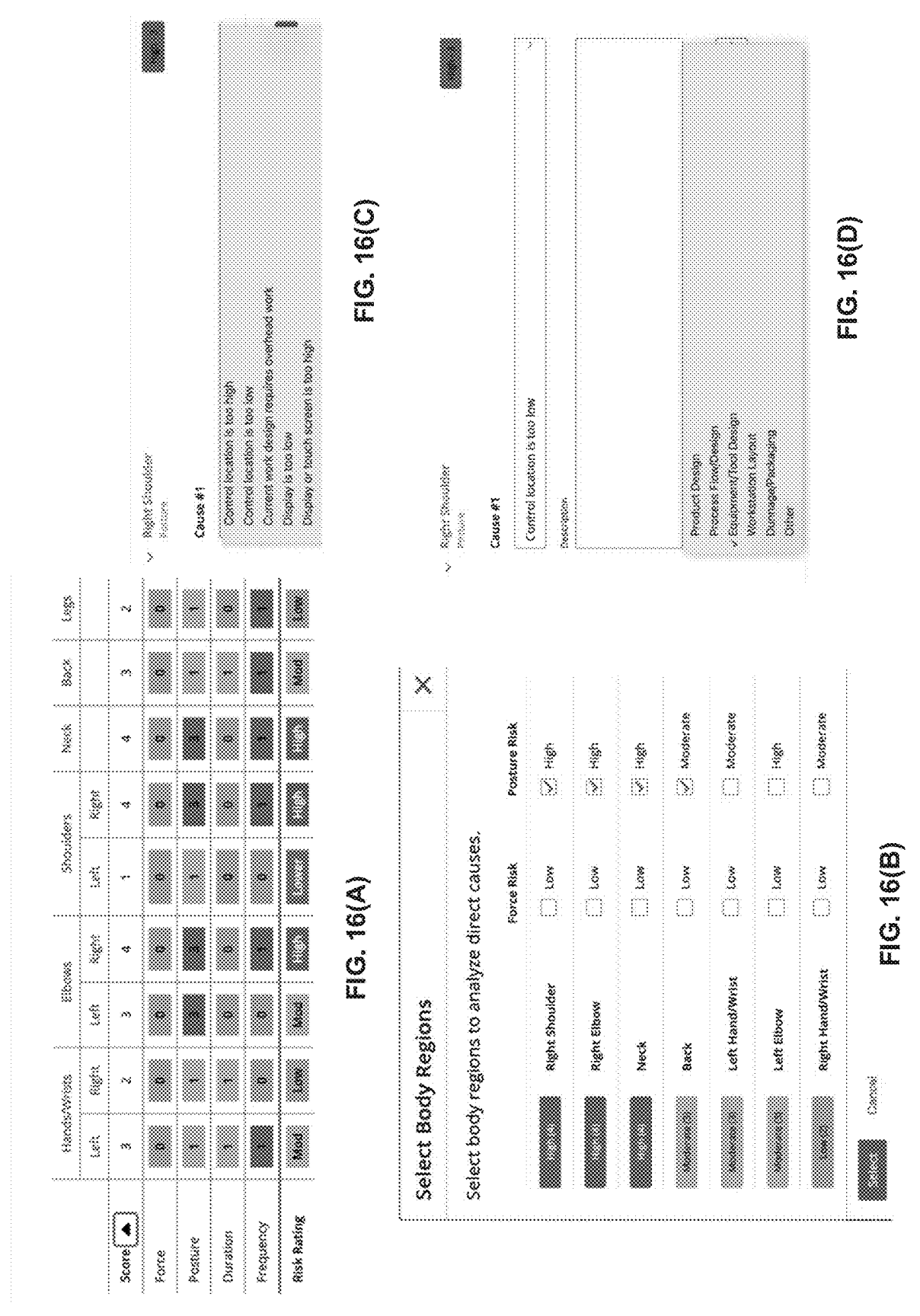

Referring to FIGS. 16(A)-16(D), the user-facing application of the system 100 may display WMSD risk root-cause analysis results by the Cloud server system 114 based at least upon video signals of a worker performing the second job related to the extracted images/frames of FIGS. 8(A)-8(D) and textual information describing a series of work activities of the job and forces being exerted during these work activities. Specifically, FIG. 16(A) illustrates the WMSD risk root-cause analysis results in a number of risk categories (e.g., "Force," "Posture," "Duration," and "Frequency") for all identified body regions (e.g., neck, back, hand/wrist, left shoulder, right shoulder, left elbow, right elbow, left knee and right knee). For each body region, a numerical risk score and the total risk rating (e.g., "Lower Risk," "High Risk," and "Higher Risk") may be calculated and displayed. The user may mark specific force and/or posture for each body region or multiple body regions on the application interface module to address and analyze the direct cause. FIG. 16(B) displays a body region selection page for detailed root-cause analysis and control suggestions. With respect to the second job (e.g., FIGS. 8(A)-8(D)), body regions that have been identified to have high or higher ergonomic risks may be further selected for direct root-cause analysis in the primary risk exposure types "Force" and "Posture." For example, in response to detecting that the user has selected "Posture Risk" analysis for the "Right Shoulder" region, one or more the direct root-causes (Level 1) may be displayed in FIG. 16(C): Control location is too high; Control location is too low; Current work design requires overhead work; Display is too low; and Display or touch screen is too high. In some embodiments, more detailed direct root-causes (Level 2) may not be generated for a selected Level 1 root-cause. As shown in FIG. 16(D), the user may further categorize the selected root-causes (e.g., "Product Design," "Process Flow/Design," "Equipment/Tool Design," "Workstation Layout," "Dunnage/Packaging," or "Other") in order to determine control suggestions. FIGS. 17(A) and 17(B) display the control suggestions and improvements to address the selected root-causes. For example, as shown in FIG. 17(A), in response to the identified root-cause that "Control location is too low" in the "Equipment/Tool Design" category, the Cloud server system 114 of the system 100 may be configured to generate a number of suggested controls including "Raise control," or any suitable "Custom Control." For each user-selected ergonomic improvement, FIG. 17(B) illustrates a number of important aspects and considerations for facilitating and managing the implementation of the improvement such as responsible personnel, cost, return on investment (ROI), control, priority, targeted date and status. The user may also add custom improvements. In one embodiment, additional information (e.g., information collected from various data sources or services 116a, 116b, 116c, . . . 116n of FIG. 1) may be presented to the user for providing or optimizing recommendations that may include text, audio, video, and other rich media explanations (e.g., a link to "Design Guidelines for Ergonomics" in FIG. 17(B)).

Figures 18A, 18B, 18C, 18D:
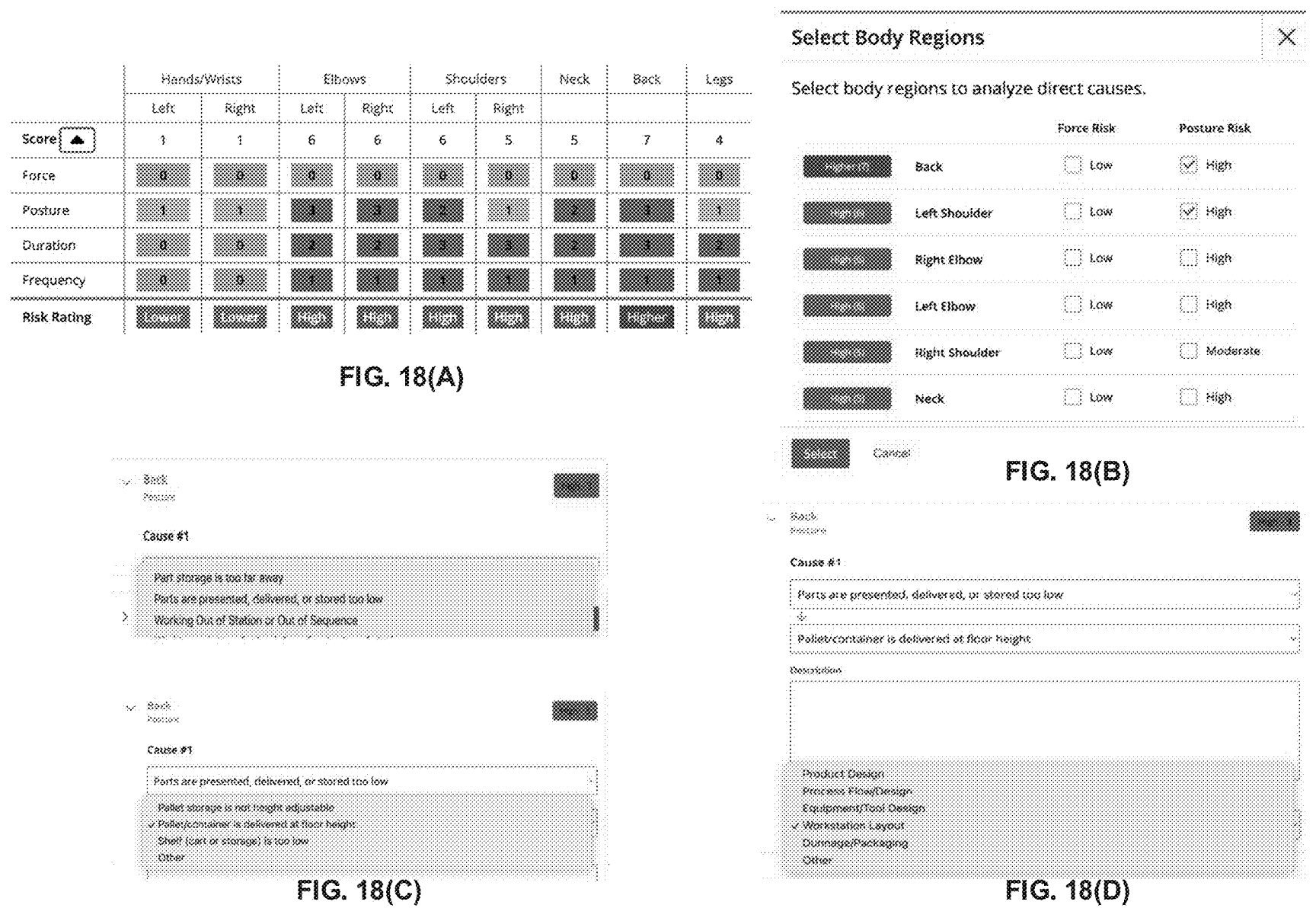

Referring to FIGS. 18(A)-18(D), the user-facing application of the system 100 may display WMSD risk root-cause analysis results by the Cloud server system 114 based at least upon video signals of a worker performing the third job related to the extracted images/frames of FIGS. 9(A)-9(D) and textual information describing a series of work activities of the job and forces being exerted during these work activities. Specifically, FIG. 18(A) illustrates the WMSD risk root-cause analysis results in a number of risk categories (e.g., "Force," "Posture," "Duration," and "Frequency") for all identified body regions (e.g., neck, back, hand/wrist, left shoulder, right shoulder, left elbow, right elbow, left knee and right knee). For each body region, a numerical risk score and the total risk rating (e.g., "Lower Risk," "High Risk," and "Higher Risk") may be calculated and displayed. The user may mark specific force and/or posture for each body region or multiple body regions on the application interface module to address and analyze the direct cause. FIG. 18(B) displays a body region selection page for detailed root-cause analysis and control suggestions. With respect to the third job (e.g., FIGS. 9(A)-9(D)), body regions that have been identified to have high or higher ergonomic risks may be further selected for direct root-cause analysis in the primary risk exposure types "Force" and "Posture." For example, in response to detecting that the user has selected "Posture Risk" analysis for the "Back" region, one or more the direct root-causes (Level 1) may be displayed in FIG. 18(C): Part storage is too far away; Parts are presented, delivered, or stored too low; and Working out of station or out of sequence. In some embodiments, more detailed direct root-causes (Level 2) may be generated for a selected Level 1 root-cause. For example, in response to detecting that the user selects "Parts are presented, delivered, or stored too low" as one of the identified root-causes for ergonomic risks associated with the third job of FIGS. 9(A)-9(D), FIG. 18(C) shows additional attributing factors such as "Pallet storage is not height adjustable," "Pallet/container is delivered at floor height," "Shelf (cart of storage) is too low," or "Other" causes defined by the user. As shown in FIG. 18(D), the user may further categorize the selected root-causes (e.g., "Product Design," "Process Flow/Design," "Equipment/Tool Design," "Workstation Layout," "Dunnage/Packaging," or "Other") in order to determine control suggestions. FIGS. 19(A) and 19(B) display the control suggestions and improvements to address the selected root-causes. For example, as shown in FIG. 19(A), in response to the identified Level 1 and Level 2 root-causes that "Parts are presented, delivered, or stored too low" and "Pallet/container is delivered at floor height" in the "Workstation Layout" category, the Cloud server system 114 of the system 100 may be configured to generate a number of suggested controls including "Provide a fixed-height pallet stand," "Provide a pallet table," "Provide a portable lift cart or pallet lift," and any suitable "Custom Control." For each user-selected ergonomic improvement, FIG. 19(B) illustrates a number of important aspects and considerations for facilitating and managing the implementation of the improvement such as responsible personnel, cost, return on investment (ROI), control, priority, targeted date and status. The user may also add custom improvements. In one embodiment, additional information (e.g., information collected from various data sources or services 116a, 116b, 116c, . . . 116n of FIG. 1) may be presented to the user for providing or optimizing recommendations that may include text, audio, video, and other rich media explanations (e.g., a link to "Design Guidelines for Ergonomics" in FIG. 19(B)).

Figures 20A, 20B, 20C, 20D:
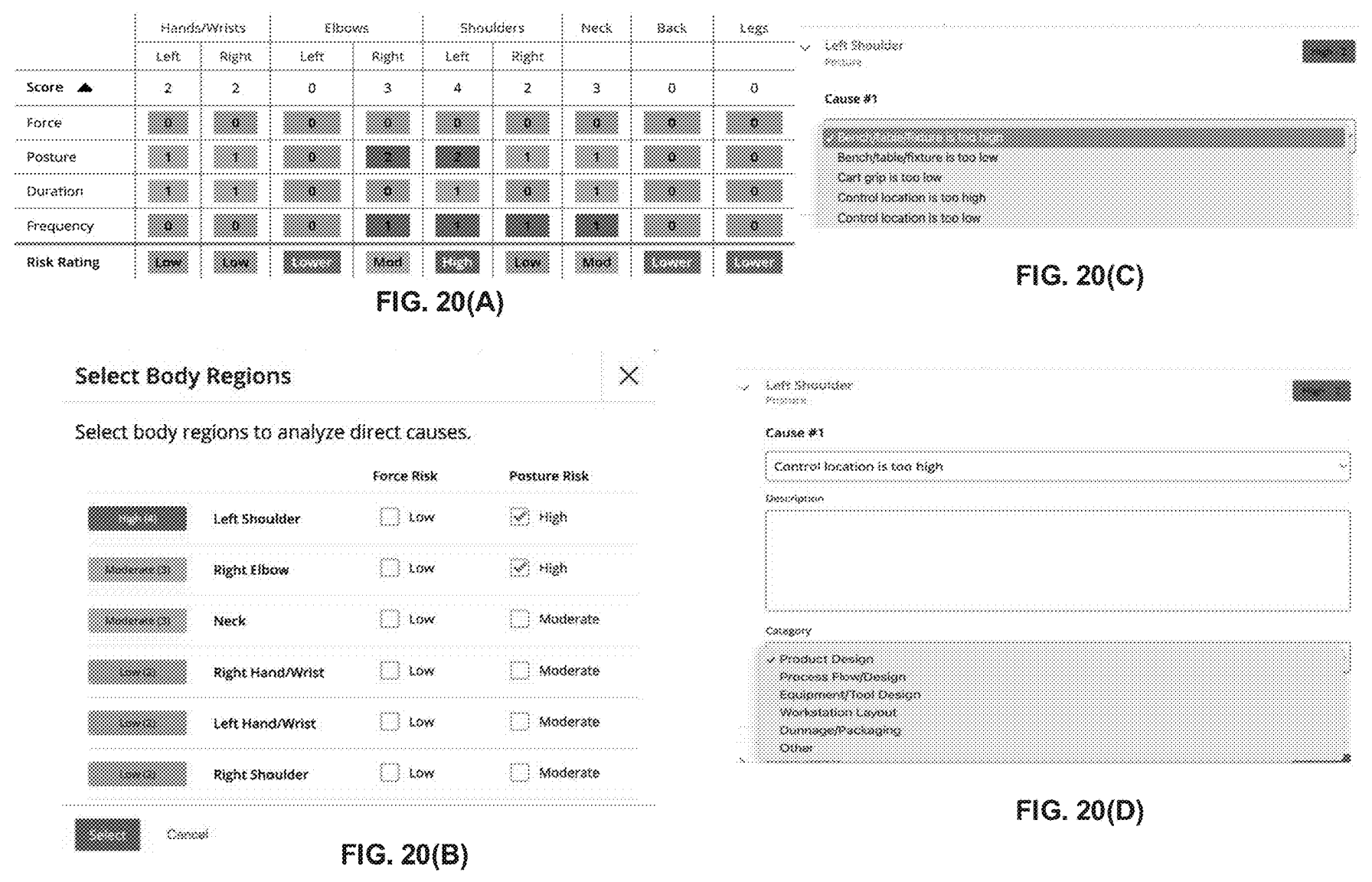
Figures 21A, 21B:
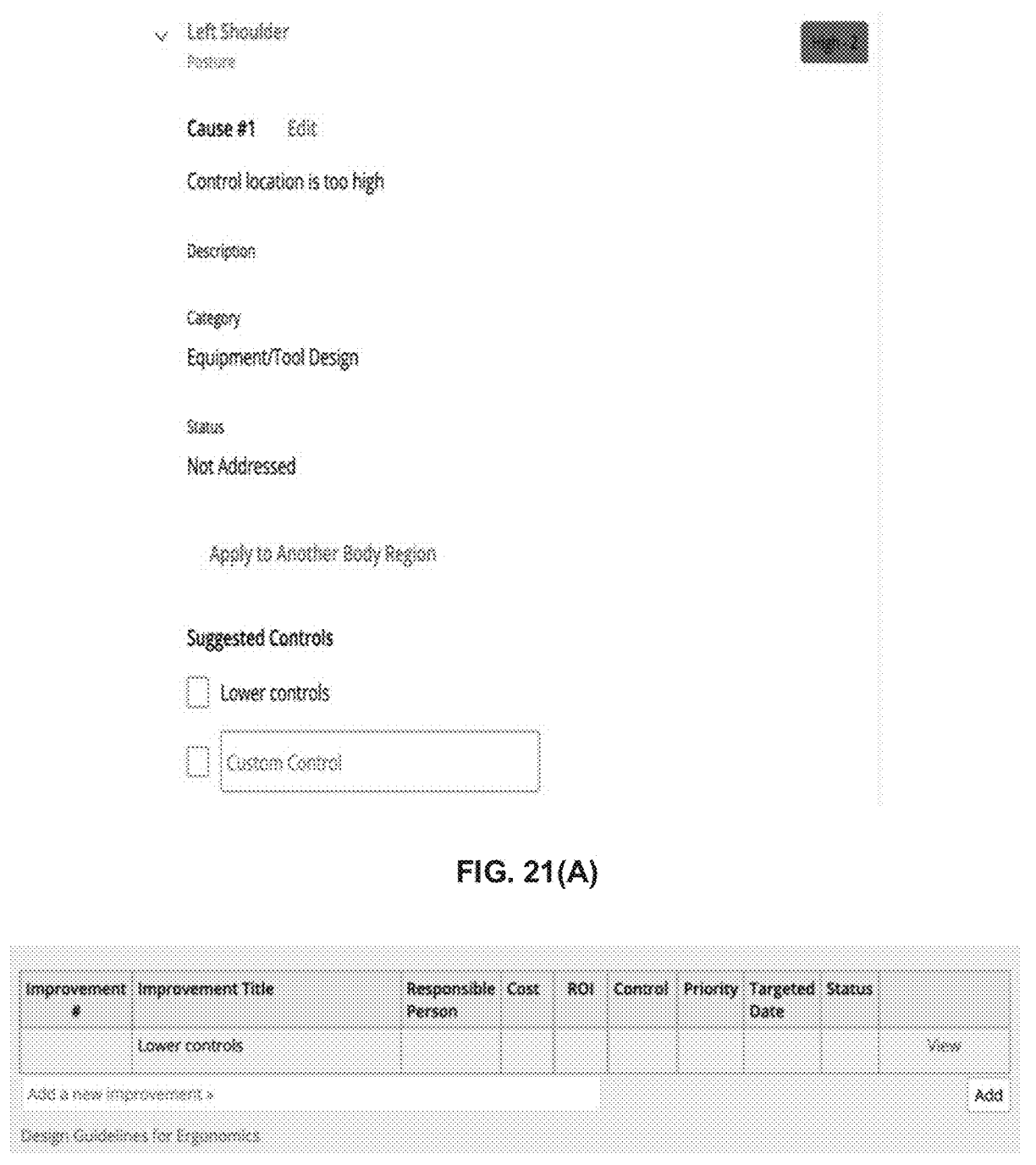

Referring to FIGS. 20(A)-20(D), the user-facing application of the system 100 may display WMSD risk root-cause analysis results by the Cloud server system 114 based at least upon video signals of a worker performing the fourth job related to the extracted images/frames of FIGS. 10(A)-10(D) and textual information describing a series of work activities of the job and forces being exerted during these work activities. Specifically, FIG. 20(A) illustrates the WMSD risk root-cause analysis results in a number of risk categories (e.g., "Force," "Posture," "Duration," and "Frequency") for all identified body regions (e.g., neck, back, hand/wrist, left shoulder, right shoulder, left elbow, right elbow, left knee and right knee). For each body region, a numerical risk score and the total risk rating (e.g., "Lower Risk," "High Risk," and "Higher Risk") may be calculated and displayed. The user may mark specific force and/or posture for each body region or multiple body regions on the application interface module to address and analyze the direct cause. FIG. 20(B) displays a body region selection page for detailed root-cause analysis and control suggestions. With respect to the fourth job (e.g., FIGS. 10(A)-10(D)), body regions that have been identified to have high or higher ergonomic risks may be further selected for direct root-cause analysis in the primary risk exposure types "Force" and "Posture." For example, in response to detecting that the user has selected "Posture Risk" analysis for the "Left Shoulder" region, one or more the direct root-causes (Level 1) may be displayed in FIG. 20(C): Bench/table/fixture is too high; Bench/table/fixture is too low; Cart grip is too low; Control location is too high; and Control location is too low. In some embodiments, more detailed direct root-causes (Level 2) may not be generated for a selected Level 1 root-cause. As shown in FIG. 20(D), the user may further categorize the selected root-causes (e.g., "Product Design," "Process Flow/Design," "Equipment/Tool Design," "Workstation Layout," "Dunnage/Packaging," or "Other") in order to determine control suggestions. FIGS. 21(A) and 21(B) display the control suggestions and improvements to address the selected root-causes. For example, as shown in FIG. 21(A), in response to the identified root-cause that "Control location is too high" in the "Equipment/Tool Design" category, the Cloud server system 114 of the system 100 may be configured to generate a number of suggested controls including "Lower controls," or any suitable "Custom Control." For each user-selected ergonomic improvement, FIG. 21(B) illustrates a number of important aspects and considerations for facilitating and managing the implementation of the improvement such as responsible personnel, cost, return on investment (ROI), control, priority, targeted date and status. The user may also add custom improvements. In one embodiment, additional information (e.g., information collected from various data sources or services 116a, 116b, 116c, . . . 116n of FIG. 1) may be presented to the user for providing or optimizing recommendations that may include text, audio, video, and other rich media explanations (e.g., a link to "Design Guidelines for Ergonomics" in FIG. 21(B)).

Figure 22:
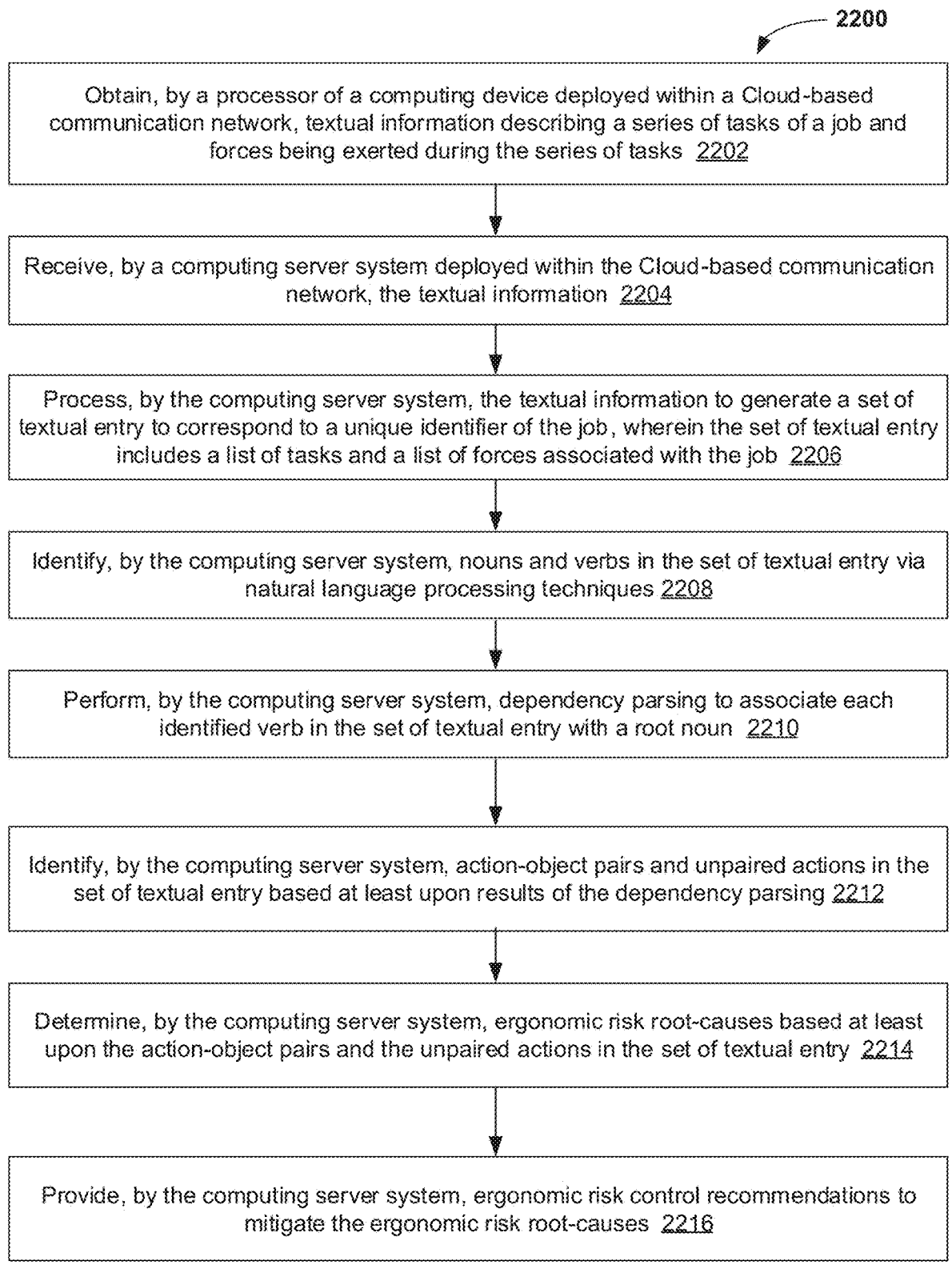
FIG. 22 illustrates a method for identifying industrial ergonomics risk root-causes and providing risk control actions, according to an exemplary aspect of the present disclosure.

According to aspects of the present disclosure, FIG. 22 illustrates a method 2200 for identifying industrial ergonomics risk root-causes and providing risk control actions. Method 2200 may comprise obtaining (2202), by a processor of a computing device deployed within a Cloud-based communication network, textual information describing a series of tasks of a job and forces being exerted during the series of tasks. A computing server system deployed within the Cloud-based communication network may be configured to receive (2204) the textual information and process (2206) the textual information to generate a set of textual entry to correspond to a unique identifier of the job, wherein the set of textual entry includes a list of tasks and a list of forces associated with the job.

The method 2200 of the present disclosure also comprises identifying (2208), by the computing server system, nouns and verbs in the set of textual entry via natural language processing techniques; performing (2210) dependency parsing to associate each identified verb in the set of textual entry with a root noun; identifying (2212) action-object pairs and unpaired actions in the set of textual entry based at least upon results of the dependency parsing; determining (2214) ergonomic risk root-causes based at least upon the action-object pairs and the unpaired actions in the set of textual entry; and providing (2216) ergonomic risk control recommendations to mitigate the ergonomic risk root-causes.

Unless specifically stated otherwise as apparent from the foregoing disclosure, it is appreciated that, throughout the present disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g.," a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

As used herein, the singular form of "a", "an", and "the" include the plural references unless the context clearly dictates otherwise.

As used herein, the term "comprising" is not intended to be limiting, but may be a transitional term synonymous with "including," "containing," or "characterized by." The term "comprising" may thereby be inclusive or open-ended and does not exclude additional, unrecited elements or method steps when used in a claim. For instance, in describing a method, "comprising" indicates that the claim is open-ended and allows for additional steps. In describing a device, "comprising" may mean that a named element(s) may be essential for an embodiment or aspect, but other elements may be added and still form a construct within the scope of a claim. In contrast, the transitional phrase "consisting of" excludes any element, step, or ingredient not specified in a claim. This is consistent with the use of the term throughout the specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. None is admitted to be prior art.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A computing server system deployed within a Cloud-based communication network, the computing server system comprising:
   a non-transitory computer-readable storage medium storing machine readable instructions; and a processor coupled to the non-transitory computer-readable storage medium and configured to execute the machine readable instructions to:
receive unstructured textual information describing a series of tasks of a job and forces being exerted during the series of tasks,
process the unstructured textual information to generate a set of textual entry,
identify nouns and verbs in the set of textual entry via natural language processing techniques,
identify action-object pairs and unpaired actions in the set of textual entry based at least upon the nouns and verbs identified in the set of textual entry,
determine ergonomic risk root-causes based at least upon the action-object pairs and the unpaired actions in the set of textual entry, and
provide ergonomic risk control recommendations to mitigate the ergonomic risk root-causes.

2. The computing server system of claim 1, wherein the unstructured textual information describing the forces being exerted during the series of tasks include at least a force direction, a force magnitude, and force textual descriptions.

3. The computing server system of claim 1, wherein the processor of the computing server system, via the machine readable instructions, is configured to determine root nouns of the nouns in the set of textual entry via part-of-speech tagging, dependency parsing, and named entity recognition.

4. The computing server system of claim 3, wherein the processor of the computing server system, via the machine readable instructions, is further configured to maintain a mapping from positions of the root nouns in the set of textual entry to the nouns.

5. The computing server system of claim 1, wherein the processor of the computing server system, via the machine readable instructions, is configured to identify the verbs in the set of textual entry via part-of-speech tagging, and perform dependency parsing to associate each identified verb in the set of textual entry with a root noun by at least determining a position of the root noun to each identified verb in a dependency tree.

6. The computing server system of claim 5, wherein the processor of the computing server system, via the machine readable instructions, is further configured to employ named entity recognition to identify one or more candidate objects based on scores determined for each candidate object, pair a candidate object having a highest score with a corresponding verb in the set of textual entry, and include the candidate object and the corresponding verb in the action-object pairs.

7. The computing server system of claim 6, wherein the processor of the computing server system, via the machine readable instructions, is further configured to identify at least one of the verbs in the set of textual entry with no associated candidate objects, and include the at least one of the verbs in the unpaired actions.

8. A computer-implemented method performed by a computing server system deployed within a Cloud-based communication network, the computer-implemented method comprising:
receiving unstructured textual information describing a series of tasks of a job and forces being exerted during the series of tasks;
processing the unstructured textual information to generate a set of textual entry;
identifying nouns and verbs in the set of textual entry via natural language processing techniques;
identifying action-object pairs and unpaired actions in the set of textual entry based at least upon the nouns and verbs identified in the set of textual entry;
determining ergonomic risk root-causes based at least upon the action-object pairs and the unpaired actions in the set of textual entry; and
providing ergonomic risk control recommendations to mitigate the ergonomic risk root-causes.

9. The computer-implemented method of claim 8, wherein the unstructured textual information describing the forces being exerted during the series of tasks include at least a force direction, a force magnitude, and force textual descriptions.

10. The computer-implemented method of claim 8, further comprising determining root nouns of the nouns in the set of textual entry via part-of-speech tagging, dependency parsing, and named entity recognition.

11. The computer-implemented method of claim 10, further comprising maintaining a mapping from positions of the root nouns in the set of textual entry to the nouns.

12. The computer-implemented method of claim 8, further comprising:
identifying the verbs in the set of textual entry via part-of-speech tagging; and
performing dependency parsing to associate each identified verb in the set of textual entry with a root noun by at least determining a position of the root noun to each identified verb in a dependency tree.

13. The computer-implemented method of claim 12, further comprising:
employing named entity recognition to identify one or more candidate objects based on scores determined for each candidate object;
pairing a candidate object having a highest score with a corresponding verb in the set of textual entry; and
including the candidate object and the corresponding verb in the action-object pairs.

14. The computer-implemented method of claim 13, further comprising identifying at least one of the verbs in the set of textual entry with no associated candidate objects, and include the at least one of the verbs in the unpaired actions.

15. A non-transitory computer readable medium storing machine executable instructions for a computing server system deployed within a Cloud-based communication network, the machine executable instructions being configured for:
receiving unstructured textual information describing a series of tasks of a job and forces being exerted during the series of tasks;
processing the unstructured textual information to generate a set of textual entry;
identifying nouns and verbs in the set of textual entry via natural language processing techniques;
identifying action-object pairs and unpaired actions in the set of textual entry based at least upon the nouns and verbs identified in the set of textual entry;
determining ergonomic risk root-causes based at least upon the action-object pairs and the unpaired actions in the set of textual entry; and
providing ergonomic risk control recommendations to mitigate the ergonomic risk root-causes.

16. The non-transitory computer readable medium of claim 15, wherein the unstructured textual information describing the forces being exerted during the series of tasks include at least a force direction, a force magnitude, and force textual descriptions.

17. The non-transitory computer readable medium of claim 16, further comprising machine executable instructions for:
   determining root nouns of the nouns in the set of textual entry via part-of-speech tagging, dependency parsing, and named entity recognition; and
   maintaining a mapping from positions of the root nouns in the set of textual entry to the nouns.

18. The non-transitory computer readable medium of claim 15, further comprising machine executable instructions for:
   identifying the verbs in the set of textual entry via part-of-speech tagging; and
   performing dependency parsing to associate each identified verb in the set of textual entry with a root noun by at least determining a position of the root noun to each identified verb in a dependency tree.

19. The non-transitory computer readable medium of claim 18, further comprising machine executable instructions for:
   employing named entity recognition to identify one or more candidate objects based on scores determined for each candidate object;
   pairing a candidate object having a highest score with a corresponding verb in the set of textual entry; and
   including the candidate object and the corresponding verb in the action-object pairs.

20. The non-transitory computer readable medium of claim 19, further comprising machine executable instructions for identifying at least one of the verbs in the set of textual entry with no associated candidate objects, and including the at least one of the verbs in the unpaired actions.

\* \* \* \* \*